United States Patent [19]
Hitchins et al.

[11] Patent Number: 6,017,330
[45] Date of Patent: Jan. 25, 2000

[54] PLUNGER SYSTEMS

[75] Inventors: Mark W. Hitchins, Sewickley; Edward J. Rhinehart, Monroeville; David M. Reilly, Glenshaw; Anthony S. McCoppin, Butler; Thomas L. Dufalla, McMurray; Robert J. Masarik, Natrona Heights, all of Pa.

[73] Assignee: Medrad, Inc., Indianola, Pa.

[21] Appl. No.: 09/239,164

[22] Filed: Jan. 28, 1999

Related U.S. Application Data

[62] Division of application No. 08/748,258, Nov. 12, 1996, Pat. No. 5,873,861.

[51] Int. Cl.⁷ .................................................. A61M 5/00
[52] U.S. Cl. ........................ 604/218; 604/131; 604/152
[58] Field of Search .................................. 604/218, 151, 604/152, 131, 232, 155, 156

[56] References Cited

U.S. PATENT DOCUMENTS

| | | |
|---|---|---|
| 3,705,582 | 12/1972 | Stumpf . |
| 3,902,491 | 9/1975 | Lajus . |
| 4,006,736 | 2/1977 | Kranys . |
| 4,180,069 | 12/1979 | Walters . |
| 4,628,969 | 12/1986 | Jurgens, Jr. . |
| 4,636,198 | 1/1987 | Stade . |
| 4,677,980 | 7/1987 | Reilly . |
| 4,705,509 | 11/1987 | Stade . |
| 4,718,463 | 1/1988 | Jurgens, Jr. . |
| 4,863,427 | 9/1989 | Cocchi . |
| 4,869,720 | 9/1989 | Chernack . |
| 4,911,695 | 3/1990 | Lindner . |
| 5,024,663 | 6/1991 | Yum . |
| 5,062,832 | 11/1991 | Seghi . |
| 5,122,118 | 6/1992 | Haber et al. . |
| 5,256,154 | 10/1993 | Liebert . |
| 5,300,031 | 4/1994 | Neer . |
| 5,314,415 | 5/1994 | Liebert . |
| 5,373,684 | 12/1994 | Vacca . |
| 5,383,858 | 1/1995 | Reilly . |
| 5,456,670 | 10/1995 | Neer et al. . |
| 5,484,413 | 1/1996 | Gevorgian . |
| 5,520,653 | 5/1996 | Reilly et al. . |
| 5,531,710 | 7/1996 | Dang . |
| 5,535,746 | 7/1996 | Hoover et al. . |
| 5,695,477 | 12/1997 | Sfikas . |

FOREIGN PATENT DOCUMENTS

| | | |
|---|---|---|
| 0 111 724 A2 | 6/1984 | European Pat. Off. . |
| 0 482 677 A1 | 4/1992 | European Pat. Off. . |

OTHER PUBLICATIONS

Drawing of Dual Flange Injector Head (publicly disclosed in July of 1995).

*Primary Examiner*—John D. Yasko
*Attorney, Agent, or Firm*—Gregory L. Bradley

[57] ABSTRACT

The plunger systems for use in an injector-actuated syringe of the present invention include a dynamic wedge seal which improves the sealing engagement between the plunger cover and syringe barrel, and flexible capture members extending from the rear surface of the plunger which permit the engagement and disengagement of the plunger from the injector drive means at any plunger position within the syringe. Further, the plunger systems include a contrast saving tip which expells the injection liquid from the syringe tip.

16 Claims, 24 Drawing Sheets

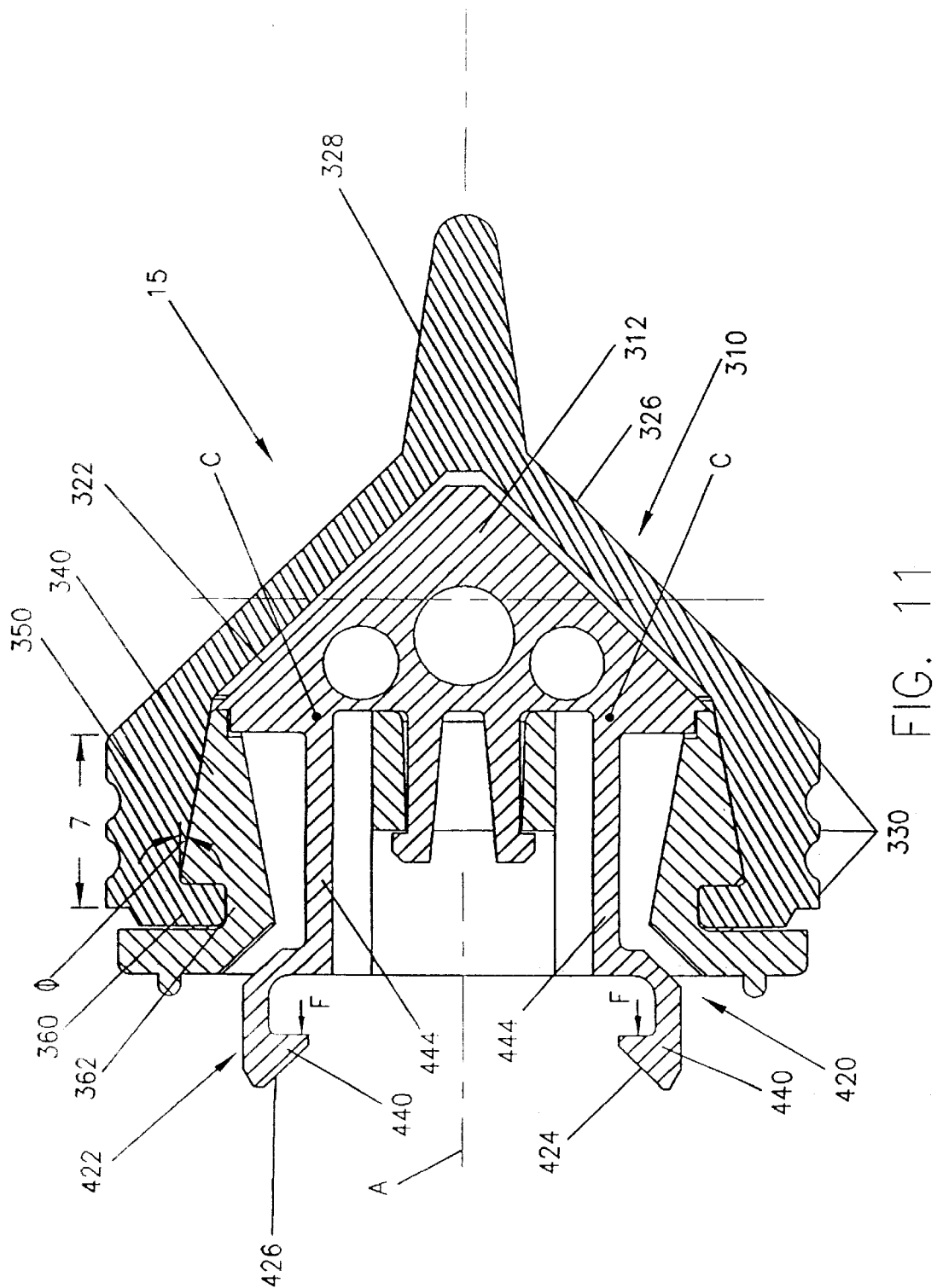

PLUNGER SYSTEMS

CROSS-REFERENCE TO RELATED APPLICATION

The present application is a divisional of application Ser. No. 08/748,258, filed on Nov. 12, 1996, now U.S. Pat. No. 5,873,861 the contents of which are hereby incorporated by reference.

FIELD OF THE INVENTION

The present invention relates to plunger systems, and more particularly to plunger systems for use with syringes and injectors.

BACKGROUND OF THE INVENTION

A number of injector-actuated syringes and powered injectors for use in medical procedures such as angiography, computer tomography and NMR/MRI, have been developed. For example, U.S. Pat. No. 4,006,736 discloses an apparatus for injecting fluid into the vascular system of a human being or an animal. Likewise, U.S. Pat. No. 4,677,980 discloses an angiographic injector and syringe wherein the drive member of the injector can be connected to, or disconnected from, the syringe plunger at any point along the travel path of the plunger via a releasable mechanism requiring rotation of the syringe plunger relative to the piston.

Numerous advances have been made in the area of injector-actuated syringes and powered injectors for use therewith. Nonetheless, newly developed and developing medical procedures constantly test the limits of current injector systems. For example, some procedures require the use of high pressures but also require physiochemical properties of the syringe (for example, chemical and biochemical compatibility with the liquid injection medium) that make attainment of high pressures difficult. Changes in syringes to meet these requirements may result in changes to the plunger used in these syringes.

It is, therefore, very desirable to develop new plunger systems for use with these new syringes.

SUMMARY OF THE INVENTION

Accordingly, the present invention provides injector-actuated syringes and injectors for use therewith that enable and/or facilitate a variety of medical procedures involving the injection of a liquid medium. In several embodiments, the present syringes and injectors enable the use of current syringe fabrication materials at higher pressures than previously attainable or the use of other fabrication materials not previously usable with high pressure-syringe and injector designs.

For example, the present invention provides generally a front-loading syringe comprising an elongated cylindrical main body and a releasable mounting mechanism. Known front-loading syringes with readily releasable mounting mechanisms are described in U.S. Pat. No. 5,383,858. The releasable mounting mechanism of the present invention comprises at least one mounting flange connected to a rear portion of the cylindrical main body and enables releasable mounting of the syringe in a desired position relative to a front wall of an injector housing. The mounting flange preferably encompasses an arcuate length equal to at least approximately one half (that is, approximately 180°) of the circumference of the rear portion of the cylindrical main body. It is understood that the mounting flange can encompass an arcuate length greater than 360° of the circumference of the rear portion of the cylindrical main body.

The releasable mounting mechanism preferably comprises more than one mounting flange. For example, the releasable mounting mechanism may comprise at least two radially projecting mounting flanges that encompass collectively an arcuate length equal to at least approximately 180° of the circumference of rear portion of the cylindrical main body. In one embodiment, the releasable mounting mechanism comprises at least a first pair and a second pair of radially projecting mounting flanges. The first pair of the mounting flanges is preferably positioned at a first axial location, and the second pair of the mounting flanges is preferably positioned at a second axial location. As set forth above, these four mounting flanges encompass collectively an arcuate length equal to at least approximately 180° of the circumference of rear portion of the cylindrical main body. It is understood that these four mounting flanges can encompass collectively an arcuate length greater than 360° of the circumference of rear portion of the cylindrical main body. Preferably, the mounting flanges of each pair of mounting flanges are positioned to be opposing (that is, positioned symmetrically with respect to each other about the axis of the cylindrical main body) to assist in eliminating uneven loading forces and torque imparted on the syringe when the injector drive member is activated.

The first pair of mounting flanges and the second pair of mounting flanges may be in general alignment. In another embodiment, the first pair of mounting flanges are offset from the second pair of mounting flanges. Preferably, the first pair of mounting flanges are offset from the second pair of mounting flanges by approximately 90°. Offsetting of the pairs of mounting flanges assists in evenly distributing forces over the entire circumference of the syringe.

The present invention also provides injectors for use with the above syringes. In general, the injectors comprise a housing having a front wall, a cooperating retainer and a powered drive member. The cooperating retainer comprises at least one slot for receiving therethrough the at least one cooperating mounting flange on the syringe. The cooperating retainer further comprises at least one retaining flange to releasably engage the at least one cooperating mounting flange over substantially the entire arcuate length of the cooperating mounting flange when the syringe is inserted into and rotated within the cooperating retainer. The syringe is thereby releasably mountable in a desired position relative to the front wall of the injector housing.

In cases in which the syringe comprises at least two mounting flanges, the cooperating retainer preferably comprises at least two slots for receiving therethrough the at least two cooperating mounting flanges on the syringe. The cooperating retainer further comprises at least two retaining flanges to releasably engage the at least two cooperating mounting flange over substantially the entire arcuate length of the cooperating mounting flanges.

In cases in which the syringe comprises multiple pairs of mounting flanges positioned at different axial positions on the syringe, but in general alignment, the cooperating retainer may comprise two slots for receiving therethrough the multiple pairs of mounting flanges on the syringe. The cooperating retainer further comprises at least one retaining flange to releasably engage each cooperating mounting flange. For example, in the case of a syringe comprising two pairs of cooperating mounting flanges, the retainer preferably comprises a first pair of retaining flanges positioned at a first axial location on the cooperating retainer to engage the first pair of opposing mounting flanges and a second pair of retaining flanges positioned at a second axial location on the cooperating retainer to engage the second pair of opposing mounting flanges.

In cases in which the syringe comprises more than two mounting flanges having offset positions on the syringe, the retainer preferably has more than two slots to receive the mounting flanges. In one embodiment described above, for example, the syringe comprises a first pair of opposing mounting flanges positioned at a first axial location on the syringe and a second pair of opposing mounting flanges being positioned at a second axial location on the syringe, the first pair of opposing mounting flanges being offset from the second pair of opposing mounting flanges by approximately 90°. For releasable mounting of such a syringe, the cooperating retainer comprises four slots (two pairs of slots offset by approximately 90°) for receiving therethrough the at least four cooperating mounting flanges on the syringe. The cooperating retainer further comprising at least four retaining flanges to releasably engage the four cooperating mounting flanges. A first pair of retaining flanges is positioned at a first axial location on the cooperating retainer to engage the first pair of mounting flanges, and a second pair of retaining flanges being positioned at a second axial location on the cooperating retainer to engage the second pair of mounting flanges. The first pair of retaining flanges are offset from the second pair of retaining flanges by approximately 90°.

The present invention also provides a number of novel syringes that expand the pressure range of syringe fabrication material for use in front-loading or rear-loading injectors. In one embodiment, the syringe comprises an elongated cylindrical main body and a generally conical transition region positioned at a end portion of the elongated cylindrical main body. The wall thickness of the conical transition region and the wall thickness of the elongated cylindrical main body are thickened in the vicinity of the intersection of the elongated cylindrical main body and the generally conical transition region (as compared to the wall thickness of the elongated cylindrical main body) to structurally reinforce the syringe in the vicinity of the intersection region to withstand relatively high internal pressures without failure. Preferably, the wall thickness of the entire conical transition region is thickened.

In another embodiment, the present invention provides a syringe for use with a powered injector comprising an elongated cylindrical main body, an elongated injection region having a diameter less than the elongated cylindrical main body and a transition region connecting the elongated cylindrical main body and the elongated ejection region. The transition region has a generally hemispherical shape to withstand relatively high internal pressures without failure.

The syringes and injectors of the present invention are particularly useful in the development of prefiflable syringes suitable to contain the injection fluid for extended periods of time. There are significant advantages, in developing syringe systems in which the syringe may be prefilled with the liquid medium to be injected. For example, use of a prefiued syringe saves the user time, minimizes the potential for mislabeling of the liquid medium, minimizes the potential of contamination of the liquid medium and also minimizes the possibility of injecting air into the patient. Current prefilled systems, such as disclosed in U.S. Pat. No. 4,628,969, require use of a pressure jacket. Such current prefilled systems are "breach-loading" and are much less convenient for the user than a front-loading system and/or a jacketless system.

The material from which such a syringe is fabricated must be compatible with the injection fluid (such as an angiography contrast medium) for extended periods of time. In other words, neither the injection fluid nor the fabrication material should detrimentally effect the performance of the other. In that regard, the fabrication material must be "chemically compatible" with the injection fluid. For example, the material for the syringe must maintain its structural integrity when in contact with the injection fluid for extended periods and must not leach any substance into the injection fluid which will impair the functionality of the injection fluid. The fabrication material must also be "biochemically compatible" with the injection fluid. For example, the fabrication material must not leach any substance into the injection fluid which will endanger the patient (animal or human) into which the injection fluid is to be injected. As used herein, the term "biochemically compatible" thus refers generally to a material that will not result in unacceptable harm to living tissue or organisms as used in connection with the present invention.

The construction material for the syringe should be chemically and biochemically compatible with the injection medium over extended periods of time. Although it is recommended that prefilled syringes be used as soon as possible after filling of the syringe, prefilled syringes preferably have a shelf life of at least approximately six (6) months. More preferably, the prefilled syringes have a shelf life of at least approximately three (3) years.

The construction material(s) for the syringe also preferably exhibit good barrier properties, for example, low water vapor transmission rate, because changes in moisture content can detrimentally affect the ionic character of certain injection fluids. Moreover, unlike syringes designed to be filled after mounting on a powered injector, prefilled syringes containing injection fluid must be sterilized. Therefore, in addition to being chemically and biochemically compatible with the injection fluid as describe above, the construction material for the syringe must exhibit physical characteristics suitable to withstand the pressures, temperatures and other forces experienced during sterilization, such as autoclave sterilization. For example, externally applied pressures of up to approximately 44–53 PSIA and temperatures of approximately 120° to 124° C. (255° F.) are often experienced during autoclave sterilization. Further, like all angiographic syringes, the material of the syringe must have physical characteristics suitable to withstand pressure and other forces experienced during injection. Finally, it is desirable that the syringe material be clear so that the injection fluid contained in the syringe can be viewed.

While certain materials exhibit suitable long-term chemical and biochemical compatibility characteristics, such materials have generally been found to be structurally weaker (that is, to have lower tensile strength and/or lower elasticity) than materials commonly used in current syringes. Examples of such current fabrication materials include polyethylene terephthalate (PET) or other dense or crosslinked plastic materials.

The novel structural changes in the syringe and injectors of the present invention enable syringes of a variety of fabrication materials to withstand the forces experienced in typical motorized injector applications. An example of a syringe fabrication material suitable for use with a variety of liquid media under the present invention is polypropylene.

The present invention also provides a plunger for use in a syringe including a dynamic seal which improves the sealing engagement between the plunger cover and syringe barrel. The syringe comprises an elongated main body, an elongated injection region having a smaller diameter than the elongated main body, and a transition region connecting the elongated main body and the elongated injection region. The plunger comprises a plunger surface or a cover surface preferably fabricated from an elastic material. In the case of a prefillable syringe, the elastic material must also be chemically and biochemically compatible with the liquid medium for extended periods of time.

The cover surface comprises a forward portion which contacts the liquid medium. The forward portion preferably has the general shape of the transition region of the syringe. The cover surface further comprises a seal portion having a generally cylindrical exterior surface. The seal portion contacts the inner wall of the elongated cylindrical main body of the syringe and forms a seal therewith. The plunger also comprises a base over which the cover surface is placed. The base comprises a forward base portion having generally the shape of the forward portion of the cover surface. The base also comprises a side portion having an angle of taper wherein the diameter of the side portion decreases from a rearward axial position to a forward axial position thereof. The diameter of an inner wall of the seal portion of the cover surface decreases from rearward to a forward axial position at an angle approximately the same as the angle of taper of the side portion of the base. The side portion of the base and the seal portion create a dynamic seal with increases of internal pressure within the syringe.

The present invention also provides a plunger comprising a releasable connection mechanism adapted to make a releasable connection with the drive member of an injector at any plunger position within the syringe barrel. The connection mechanism comprises at least two relatively flexible capture members projecting rearwardly from a rear surface of the plunger. The capture members flex radially outwardly when contacted by a forward, relatively rigid piston head of the drive member during forward advancement of the piston head to form a releasable connection with the piston head. The drive member of the injector preferably comprises a piston including a piston head positioned at forward end thereof The piston head is preferably formed of a relatively rigid material. Preferably, the capture members include shoulders or abutment surfaces that abut the piston head to prevent disengagement of the piston head and the capture members upon rearward motion of the piston. The plunger is preferably readily releasable from the piston head upon relative rotation of the plunger and the piston head, such that the piston head is no longer abutted by the abutment shoulders, thus permitting subsequent rearward motion of the piston without retracting the plunger. Known readily releasable mechanisms are described in U.S. Pat. Nos. 4,677,980 and 5,383,858.

In an alternative embodiment, the capture members are rigid and the piston head comprises flexible members which flex to allow capture and retention thereof by the capture member. Once again, the plunger is preferably readily releasable from the piston head upon relative rotation of the plunger and the piston head.

Finally, the present invention provides a plunger that results in less waste of contrast medium than current plunger designs. Numerous syringes comprise an elongated main body, an elongated injection region having a smaller diameter than the elongated main body, and a transition region connecting the elongated main body and the elongated injection region. The plunger of the present invention comprises a cover surface including a forward portion which contacts the liquid medium. The cover surface also comprises a protruding member at a forward end of the forward portion. The protruding member is adapted to enter the elongated injection region of the syringe when the plunger is advanced to expel liquid medium contained in the elongated injection region. The forward portion preferably has, for example, a generally conical shape or a generally hemispherical shape depending on the shape of the transition region of the syringe.

BRIEF DESCRIPTION OF THE DRAWINGS

Other aspects of the invention and their advantages will be discerned from the following detailed description when read in connection with the accompanying drawings, in which:

FIG. 11 illustrates a cross-sectional view of a plunger of the present invention;

DETAILED DESCRIPTION OF THE INVENTION

Figure 1A:
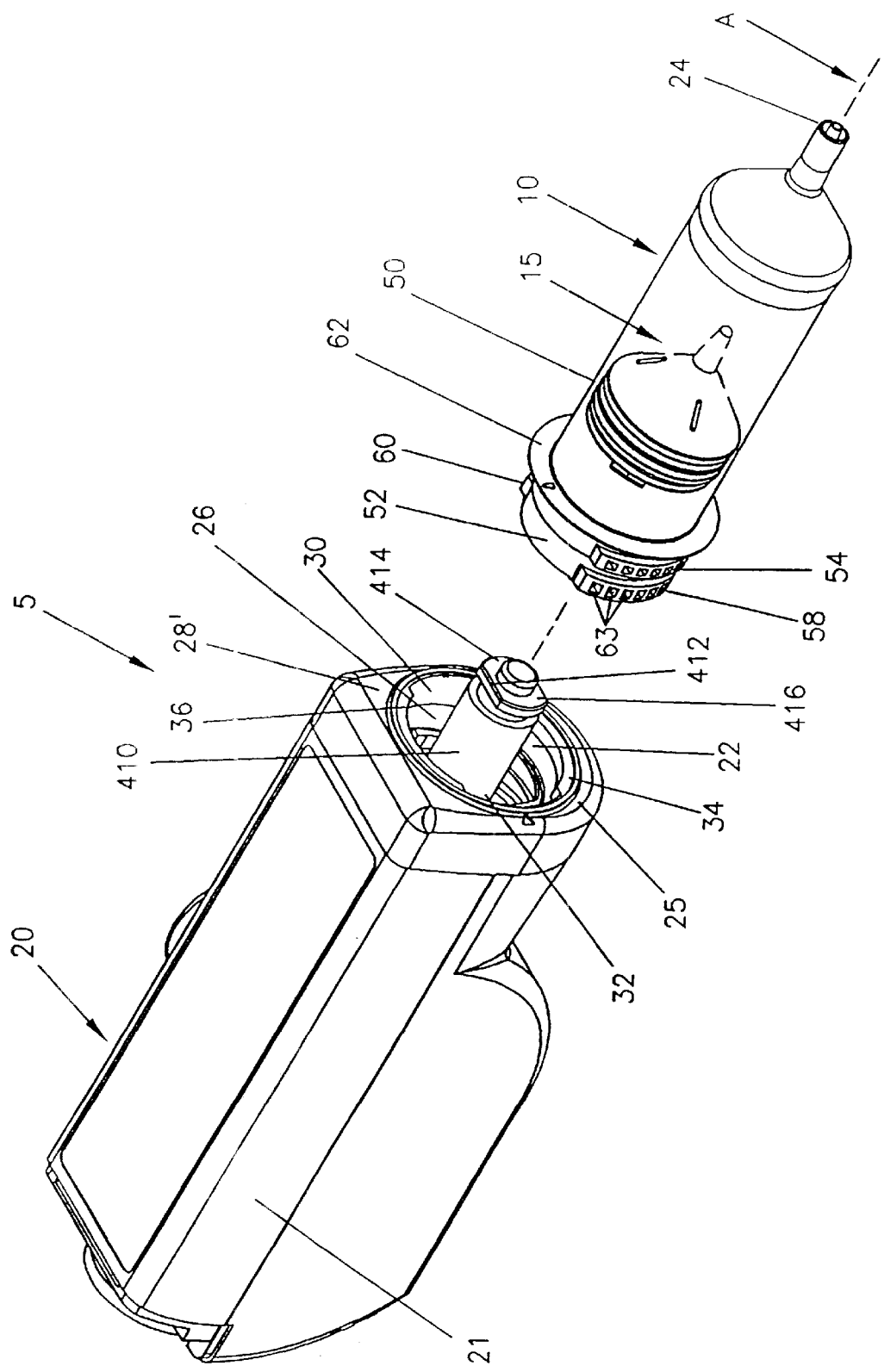
FIG. 1A illustrates an embodiment of an injector system of the present invention in which the syringe comprises two pairs of mounting flanges in general alignment.
Figure 1B:
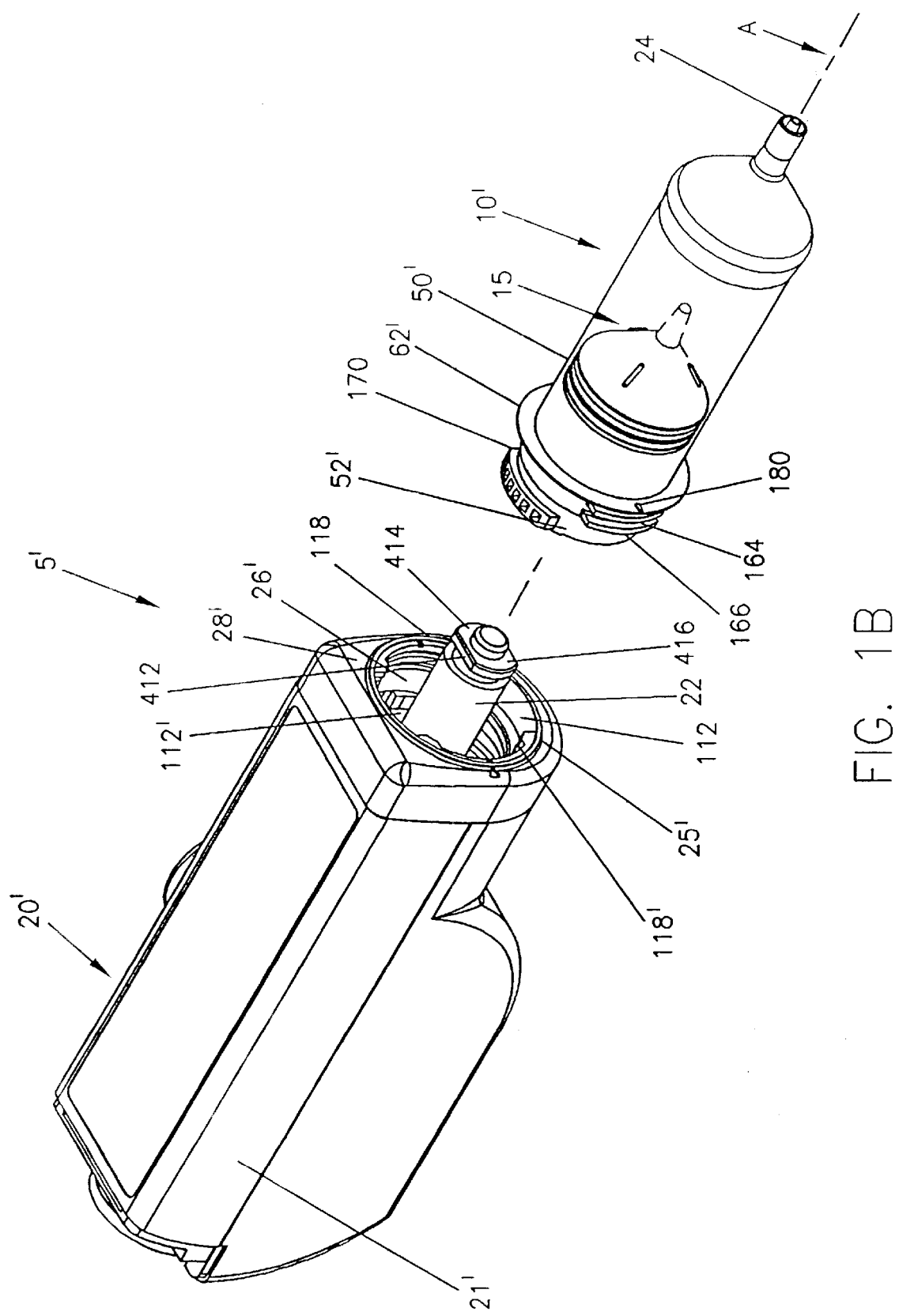
FIG. 1B illustrates an embodiment of an injector system of the present invention in which the syringe comprises two pairs of radially offset mounting flanges.

Two embodiments of front-loading injector systems 5 and 5' of the present invention are illustrated in FIGS. 1A and 1B, respectively. A front-loading syringe and injector system is also disclosed in U.S. Pat. No. 5,383,858, the disclosure of which is incorporated herein by reference. Injector systems 5 and 5' generally differ substantially only in the manner in which the syringes are mounted upon the corresponding injector. Like entities in each of systems 5 and 5' are numbered the same.

Injector system 5 includes an injector 20 and a syringe 10. Injector housing 21 of injector 20 preferably includes a reciprocating piston 22 therein which cooperates with a syringe plunger 15 to inject an injection fluid or liquid medium from the interior of syringe 10 into a patient. Piston 22 is extendible and retractable via a powered means preferably contained within injection housing 21 and comprising, for example, a motor or hydraulic system, including appropriate gearing (not shown). As known in the art, injector housing 21 also preferably includes a motor controller for controlling operation of a motor and thereby controlling operation of piston 22.

As used herein to describe systems 5 and 5', the terms "axial" or "axially" refer generally to an axis A around which systems 5 and 5' (including, for example, piston 22 and syringes 10 and 10') are preferably formed (although not necessarily symmetrically therearound). The terms "proximal" or "rearward" refer generally to an axial direction toward the end of injector housing 21 opposite the end to which syringe 10 is mounted. The terms "distal" or "forward" refer generally to an axial direction toward a syringe tip 24 of syringe 10. The term "radial" refers generally to a direction normal to axis A.

Referring to FIG. 1A, piston 22 moves axially forwardly and rearwardly through a retainer 25 comprising an opening 26 formed in a front wall 28 of injector housing 21. Opening 26 and syringe 10 preferably comprise cooperating means for securely affixing syringe 10 to front wall 28. Preferably, such securing means comprise a cooperating mounting mechanism formed upon the rearward portion of syringe 10 and a cooperating retainer 25 formed upon injector front wall 28.

Figure 2A:
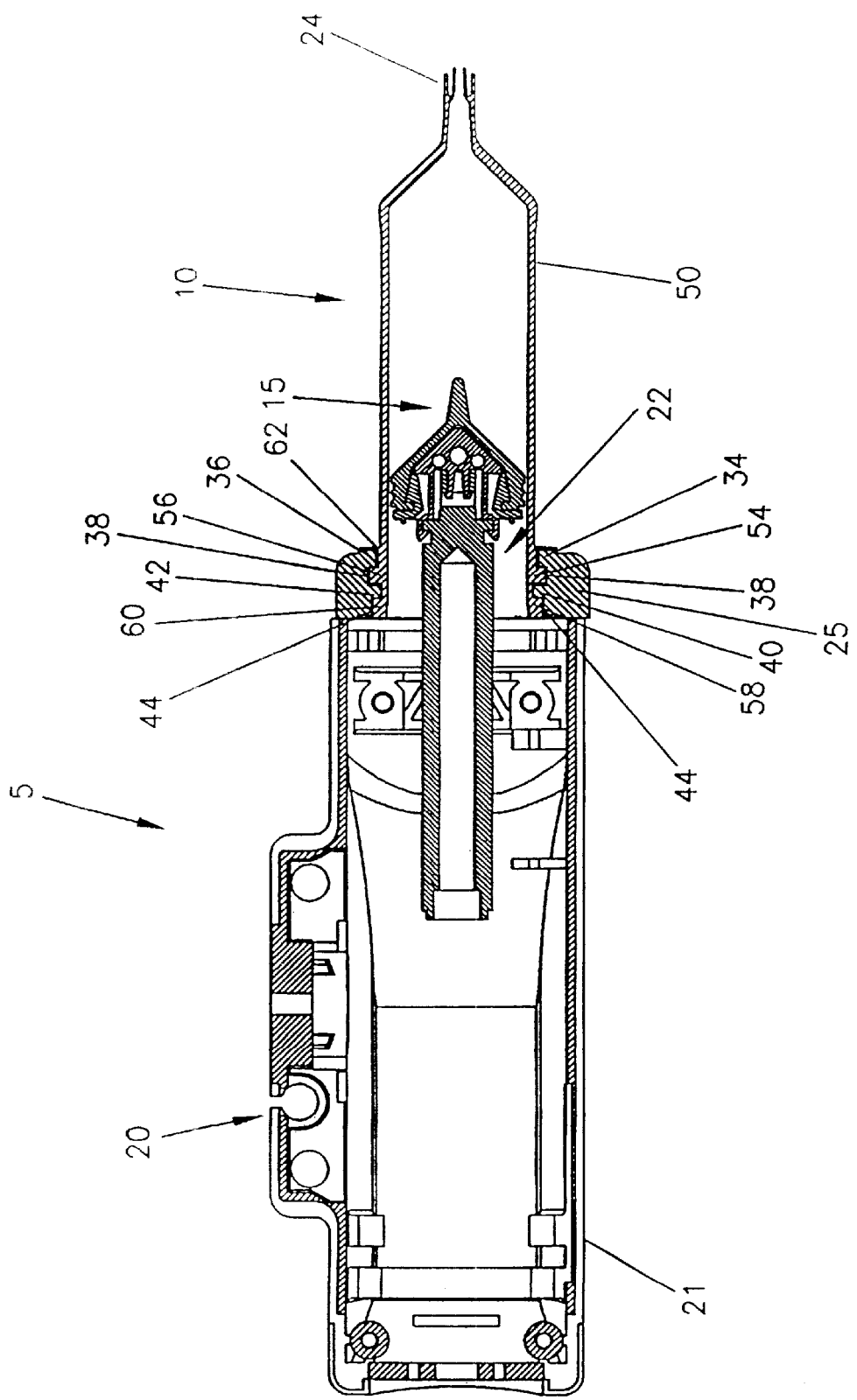
FIG. 2A illustrates an axial cross section of the injector system of FIG. 1A.
Figure 3A:
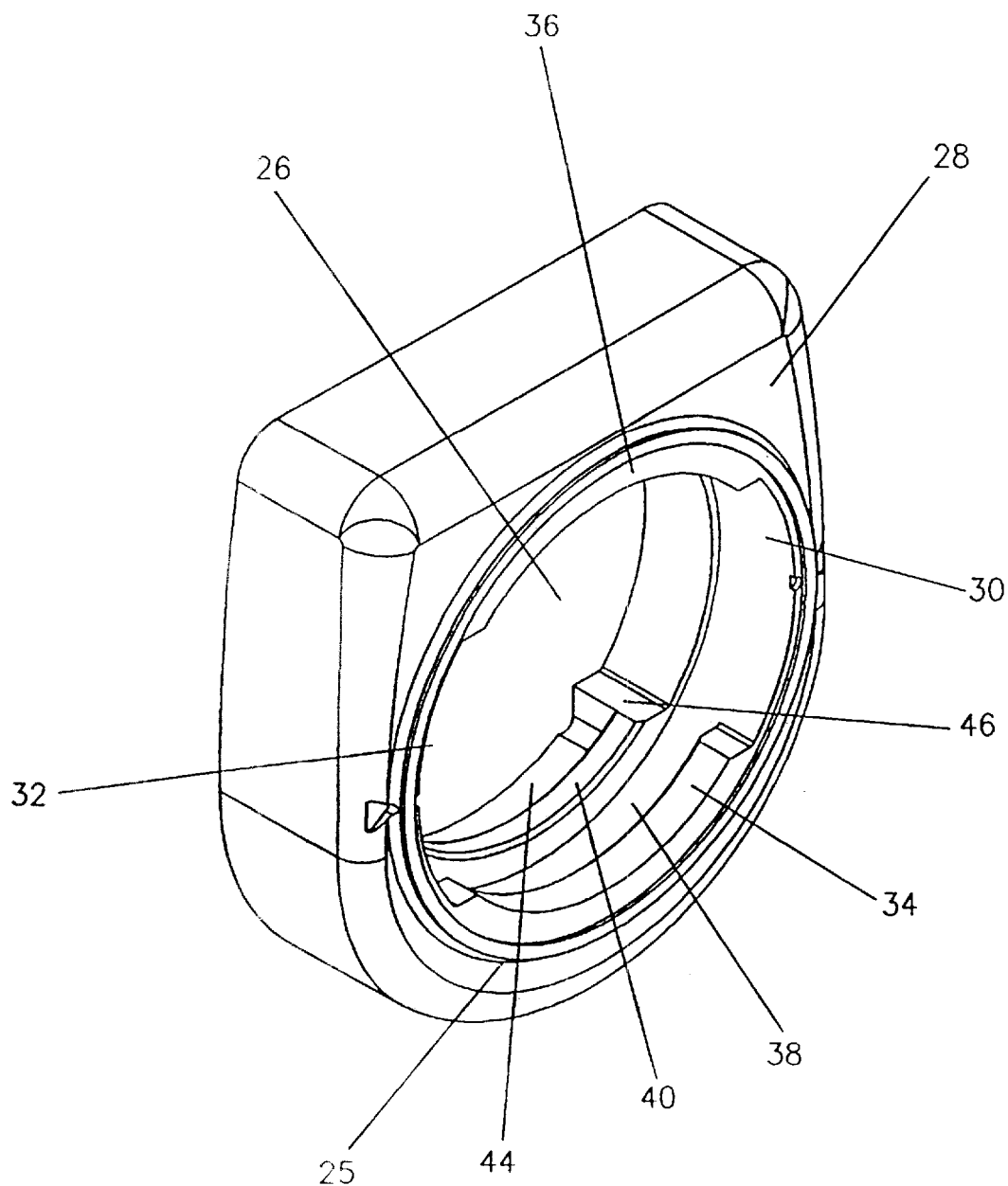
FIG. 3A illustrates a front elevational view of the front wall of FIG. 1A.

In the embodiment of FIGS. 1A, 2A and 3A, opening 26 comprises a pair of opposed, axially extending slots 30 and 32. Slots 30 and 32 preferably separate and define a first pair of radially inwardly projecting syringe retaining flanges 34 and 36 formed around the circumference of the opening 26. To the rear of first retaining flanges 34 and 36 is a first circumferential groove or channel 38, which is in communication with the axial slots 30 and 32.

As shown in FIG. 3A, to the rear of channel 38, are preferably a pair of second, radially inwardly projecting retaining flanges 40 and 42. Retaining flange 42 is shown in FIG. 2A, and is preferably substantially identical to retaining flange 40. Retaining flanges 34 and 40 are preferably generally symmetrically aligned with retaining flanges 36 and 42, respectively, about axis A. A second circumferential channel 44 (see FIG. 2A), also in communication with slots 30 and 32, is preferably formed between the rear radial sidewalls of mounting flanges 40 and 42 and a rear abutment member 46. Retainer 25 (including first retaining flanges 34 and 36 and second retaining flanges 40 and 42) is preferably formed as a portion of injector front wall 28.

Front wall 28 and retainer 25 may, for example, be machined out of aluminum or other suitable material such as plastic. Certain plastics may be preferable because of their "low friction" characteristics. In that regard, the relatively large surface of the mounting flanges and the drip flange of the present syringes may result in significant friction when installing the syringe in the injector. Any material suitable to lower frictional forces would be beneficial. Plastics such as polyacetal may offer such a benefit.

Opening 26 of retainer 25 receives and firmly secures syringe 10 to injector front wall 28. In that regard, syringe 10 preferably comprises an elongated, generally cylindrical body 50 including a rear portion 52 which preferably includes a first set of radially extending mounting flanges 54 and 56 and a second set of radially extending mounting flanges 58 and 60. A radially extending drip flange 62 is preferably formed forwardly from first mounting flanges 54 and 56 on body 50. Drip flange 62 assists in proper axial positioning of syringe 10 with respect to front wall 28 by preferably abutting the face of front wall 28 when syringe 10 is properly positioned. Drip flange 62 further substantially prevents liquid from leaking into injector housing 21. Such leakage into injector housing 21 may cause damage to injector 20. Drip flange 62 also provides structural reinforcement for syringe body 50. As illustrated, syringe 10 is preferably formed around axis A such that its components are generally symmetrical with respect to axis A.

The structure of second mounting flanges 58 and 60 is preferably similar to the structure of first mounting flanges 54 and 56. Each of first mounting flanges 54 and 56 and second mounting flanges 58 and 60 preferably includes a plurality of ribs 63. In the embodiment of FIGS. 1A, 2A and 3A, ribs 63 provide improved strength at reduced material cost and minimize the potential for material shrinkage that can occur during injection molding.

During mounting of syringe 10 in front wall 28, first mounting flanges 54 and 56 of the syringe 10 are preferably rotatably and closely received in first circumferential channel 38 to be retained by first retaining flanges 34 and respectively 36. Second mounting flanges 58 and 60 are preferably similarly received in second channel 44 to be retained by second retaining flanges 40 and 42, respectively.

First channel 38 is preferably dimensioned differently from (for example, deeper and/or narrower than) second channel 44. Accordingly, first mounting flanges 54 and 56 are correspondingly narrower and/or more radially extensive than second mounting flanges 58 and 60. The dimensional differences in the mounting flanges and their respective channels substantially prevent mis-mounting or partial mounting of syringe 10 in retainer 25. For example, if the user mistakenly aligns second retaining flanges 58 and 60 with first channel 38 and attempts to rotate second mounting flanges 58 and 60 behind first retaining flanges 34 and 36, the dimensions of channel 38 will prevent such rotation. The user must (1) insert syringe 10 rearwardly to abut a stop member or such that drip flange 62 abuts the front face of front wall 28 and then (2) rotate syringe mounting flanges 56, 54, 58 and 60 relative to retainer 25 so that they will occupy the channels, immediately behind respective retaining flanges 34, 36, 40 and 42. In this way, both sets of syringe mounting flanges will be securely and fully engaged and available to resist forward force exerted on syringe 10 by piston 22.

The mounting flanges and corresponding retaining flanges must provide enough area of contact to adequately retain syringe 10 without mechanical failure during injection procedures. Preferably, one or more mounting flanges are provided around the circumference of the rear portion of syringe 10 such that the one or more flanges encompass cumulatively an arcuate length equal to at least approximately one-half of the circumference of the rear portion of syringe 10 (that is, approximately 180°). This result may be accomplished using multiple flanges as described above or using a single helical or screw-like flange (not shown). It is understood that the one or more mounting flanges may encompass cumulatively an arcuate length greater than 360° of the circumference of the rear portion of syringe 10. The one or more mounting flanges are preferably positioned symmetrically around the body of syringe 10, however, to prevent unequal flange loading or torque when piston 22 engages plunger 15 to push plunger 15 forward.

In the embodiment illustrated in FIG. 1A, first pair of mounting flanges 54 and 56 are in general alignment with second pair of mounting flanges 58 and 60. In an alternative embodiment (not shown), the centers of the first pair of mounting flanges 54 and 56 are positioned or rotated approximately 90° from the centers of second pair of mounting flanges 58 and 60. In the corresponding injector, the center of channel 38 is positioned or rotated approximately 90° from the center of channel 44, and the center of retaining flange 34 is positioned or rotated approximately 90° from the center of retaining flange 40, so as to accomotate the offset syringe mounting flanges 54 and 56, and 58 and 60. The benefits of offsetting the centers of the syringe mounting flanges are discussed below in connection with the embodiment shown in FIGS. 1B, 2B and 3B.

Figure 2B:
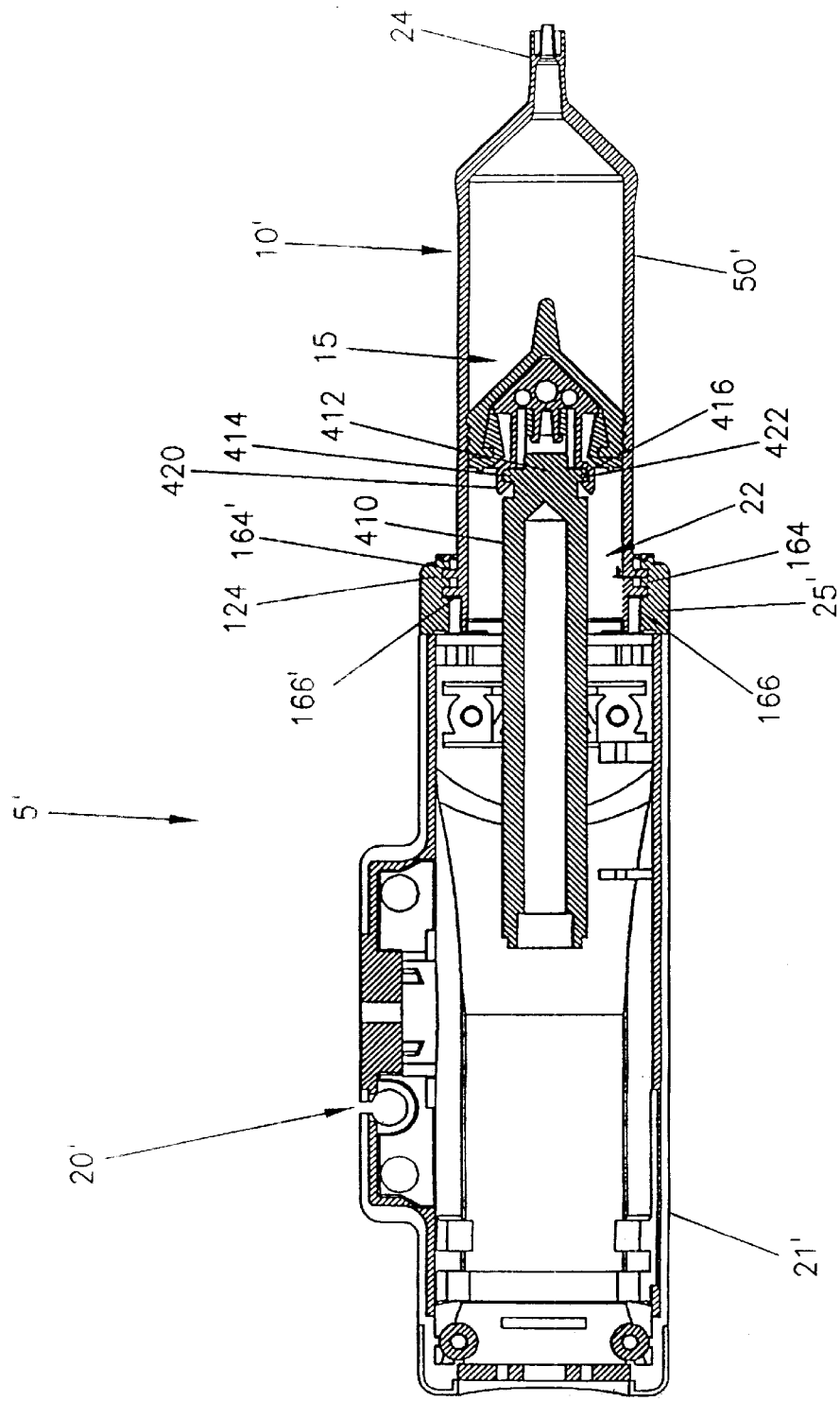
FIG. 2B illustrates an axial cross section of the injector system of FIG. 1B.
Figure 3B:
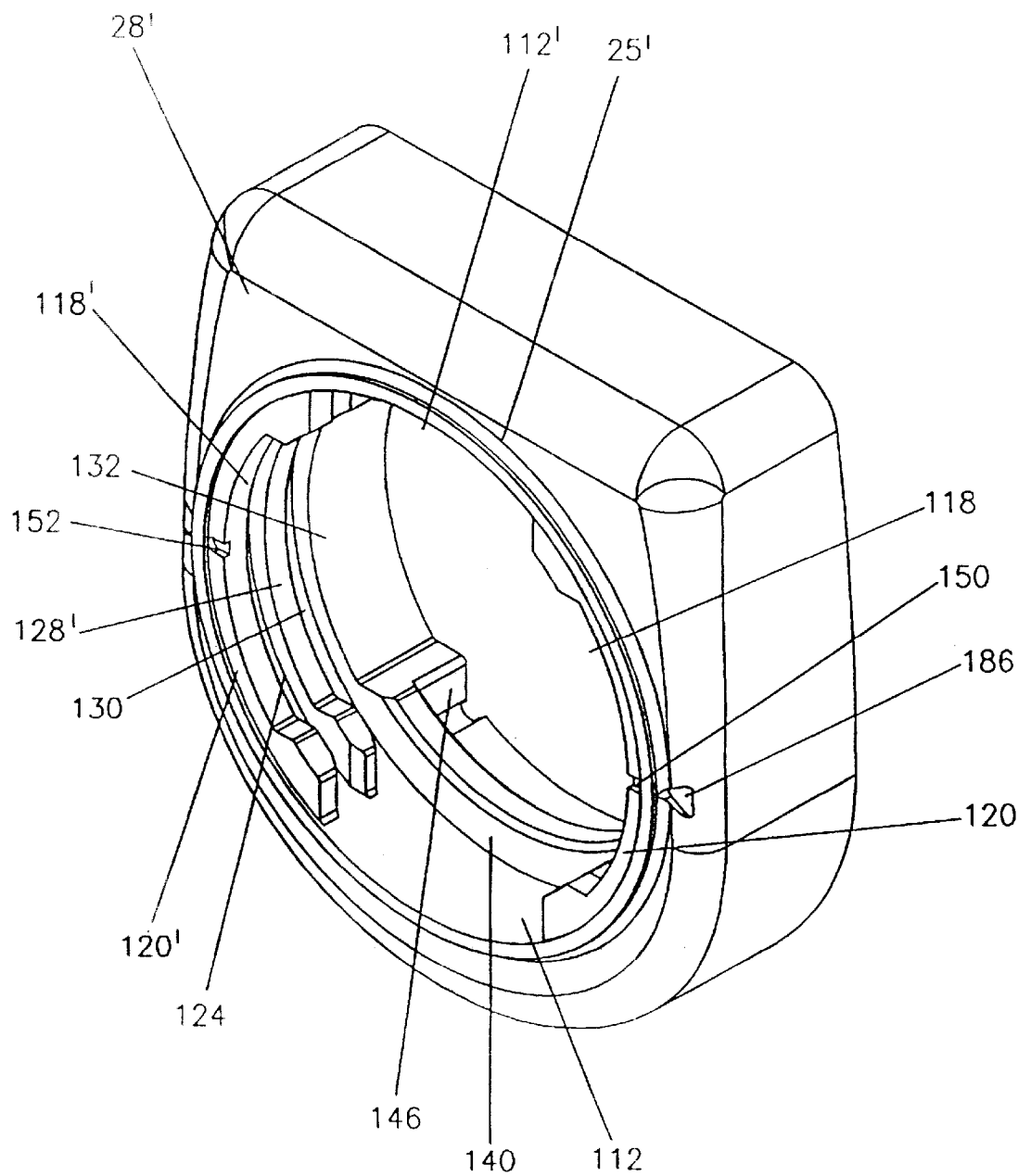
FIG. 3B illustrates a front elevational view of the front wall of FIG. B.

In the embodiment of injector system 5', as best illustrated in FIGS. 1B, 2B and 3B, opening 26' comprises two pairs of opposed, axially extending slots 112 and 112' and 118 and 118'. The centers of first pair of slots 112 and 112' are positioned or rotated approximately 90° from the centers of second pair of slots 118 and 118'. Slots 112 and 112' preferably separate and define at least a first pair of radially inwardly projecting syringe retaining flanges 120 and 120' formed around the circumference of the opening 26'. To the rear of first retaining flanges 120 and 120' is a first circumferential groove or channel 124, which is in communication with the axial slots 112 and 112'.

To the rear of channel 124, are preferably a pair of second, radially inwardly projecting retaining flanges 128 and 128'. Retaining flanges 128 and 128' are preferably generally aligned with retaining flanges 120 and 120'. Retaining flange 128 is not shown in FIG. 3B, but is identical to retaining flange 128'. A second circumferential channel 130 (preferably also in communication with slots 112 and 112') is preferably formed between the rear of mounting flanges 128 and 128' and a rearward ledge 132 (see FIG. 3B).

Figure 4:
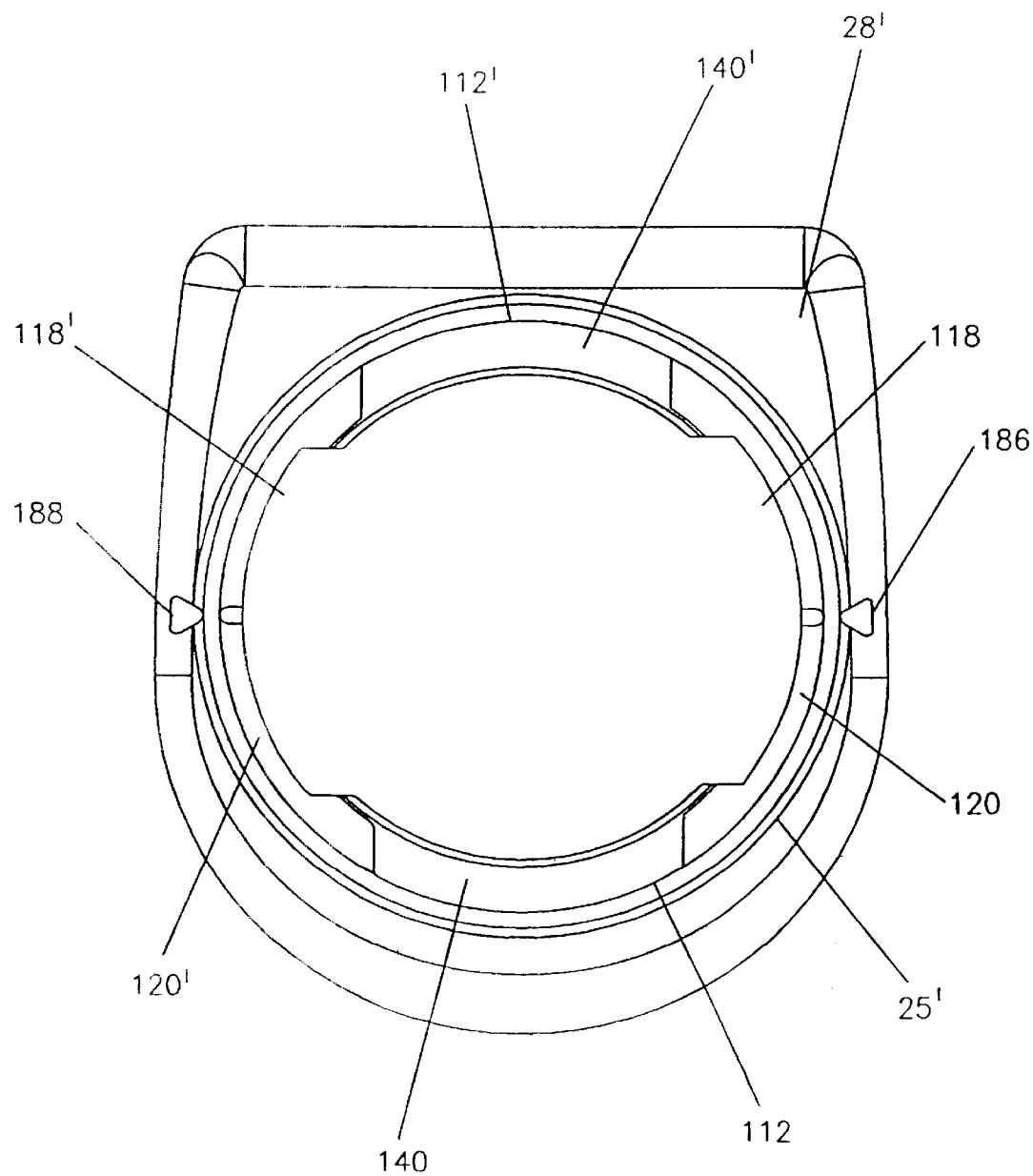
FIG. 4 illustrates a front view of the front wall of FIG. 3B.

Slots 118 and 118' are preferably formed as radially inward projecting slots in retaining flanges 120 and 120' and 128 and 128'. Preferably, the depth of slots 118 and 118' is somewhat less that the radial width of retaining flanges 120 and 120'. As shown in FIG. 4, slots 118 and 118' preferably separate and frame at least third pair of radially inwardly projecting syringe retaining flanges 140 and 120' formed around the circumference of the opening 26' and 128 and 128'.

Syringe 10' preferably comprises a body 50' comprising a rear portion 52' which preferably includes a first pair of radially extending mounting flanges 164 and 164' and a second pair of radially extending mounting flanges 166 and 166'. A radially extending drip flange 62' is preferably formed forwardly from first mounting flanges 164 and 164' on body 50'. First mounting flanges 164 and 164' and second mounting flanges 166 and 166' are preferably in general alignment. The structure of second mounting flanges 166 and 166' is preferably similar to the structure of first mounting flanges 164 and 164'.

In the case of some fabrication materials, uneven distribution of forces over the circumference of the syringe 10' can result in undesirably quick failure of the syringe 10'. Therefore, syringe body 50' also preferably comprises a third pair of radially extending mounting flanges 170 and 170'. The centers of third mounting flanges 170 and 170' are preferably offset or rotated approximately 90° (around axis A) from the centers of first mounting flanges 164 and 164'. Thus, offsetting of mounting flanges, as illustrated in FIG. 1B, assists in evenly distributing forces over the circumference of syringe 10'.

As described above for injector system 5, opening 26' receives and firmly secures syringe 10' to injector front wall 28'. During mounting, third pair of mounting flanges 170 and 170' pass through second pair of slots 118 and 118', respectively. First pair of mounting flanges 164 and 164' and second pair of mounting flanges 166 and 166' pass through first pair of slots 112' and 112, respectively. Upon, for example, abutment of drip flange 62' with the face of front wall 28', syringe 10' is rotated clockwise relative to retainer 25' approximately 90° to firmly and releasably mount syringe 10' on injector housing 21' of injector 20'. To release syringe 10' from injector 20', the process of mounting is simple reversed.

The distinctive positioning and sizing of the mounting flanges and corresponding retainers of systems 10 and 10' substantially ensure proper axial mounting alignment. Systems 10 and 10' are preferably also provided with one or more means for ensuring that syringes 10 and 10' are properly and securely rotatably mounted in retainers 25 and 25', respectively. Referring to FIG. 3A, for example, second channel 44 preferably terminates in a transverse stop 46 to abut an edge of one of second mounting flanges 58 and 60 upon full rotation of syringe 10. Likewise, and referring to FIG. 3B retainer 25' preferably includes a transverse stop 146 to abut an edge of one of third mounting flanges 170 and 170' upon full rotation of syringe 10'.

Another means of ensuring proper engagement of the syringe mounting flanges behind their corresponding retaining flanges is to provide means for providing feedback to a user once proper engagement has been effected. Such feedback may be audio, visual and/or tactile. For example, indentations 150 and 152 (see FIG. 3B) may be provided on retainer 25' of injector front wall 28' to receive corresponding projections 156 and 158 formed on the rear surface of drip flange 62' (see FIG. 6A). Projections 156 and 158 fall into place within indentations 150 and 152 to create an audible "click" sound when syringe 10' is properly secured.

Figure 8:
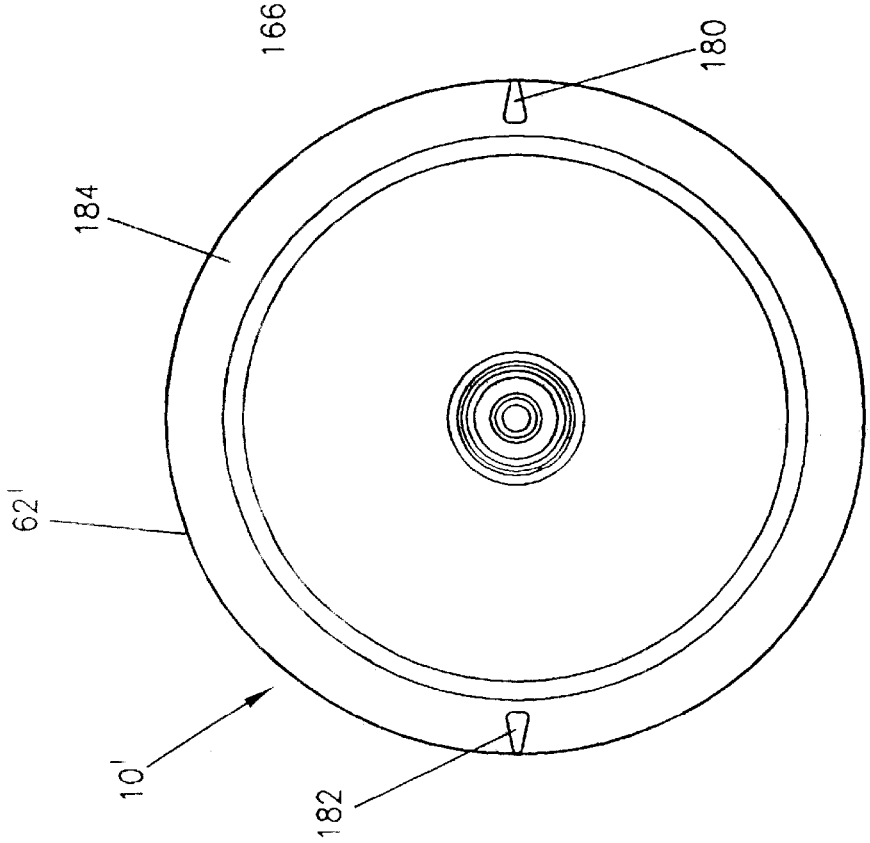
FIG. 8 illustrates a front view of the syringe of FIG. 7A.
Figure 10:
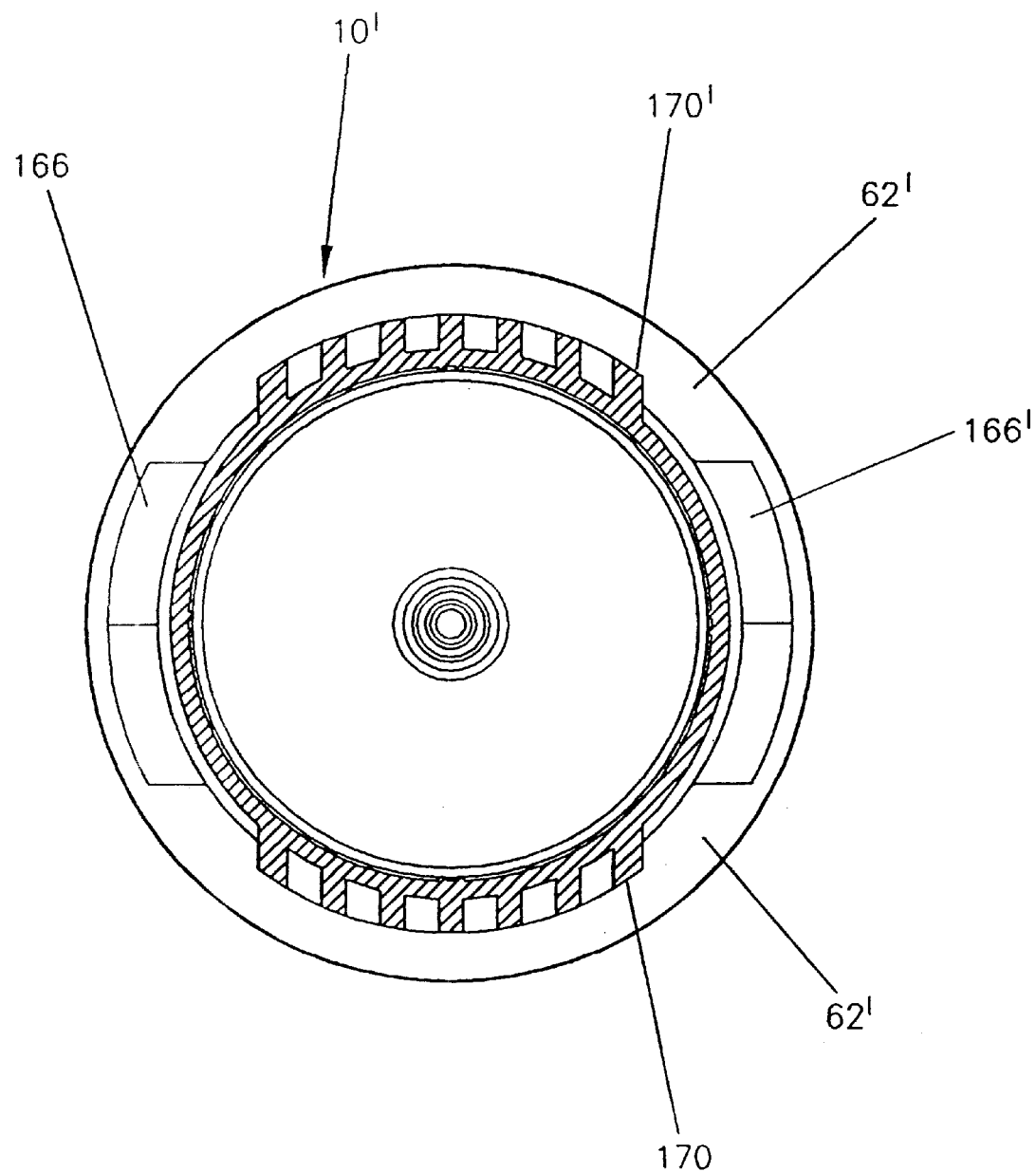
FIG. 10 illustrates a rear, partially cross-sectional view of the syringe of FIG. 7A.
Figure 12A:
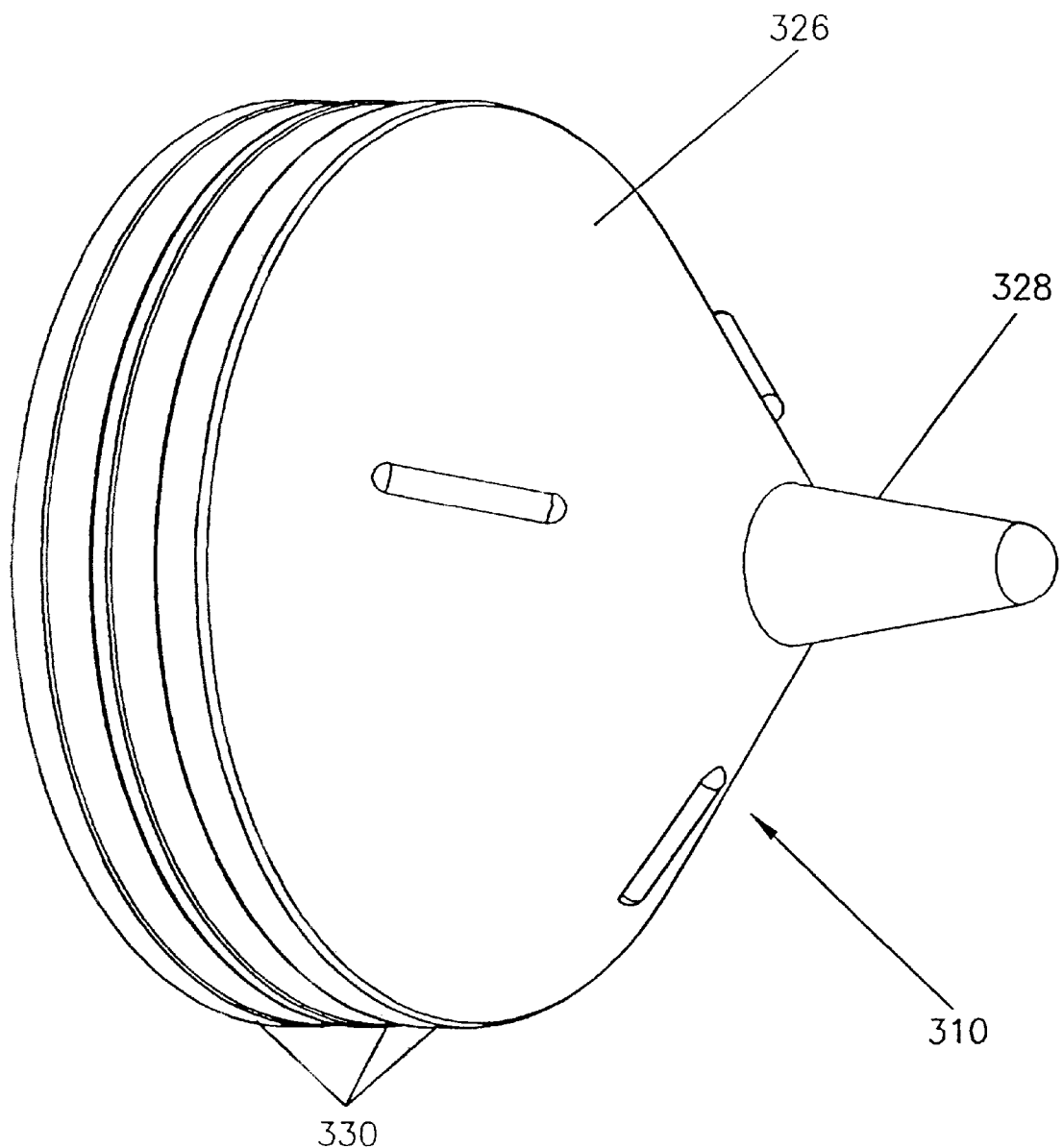
FIG. 12A illustrates an elevational view of an embodiment of a cover surface of a plunger of the present invention.
Figure 12B:
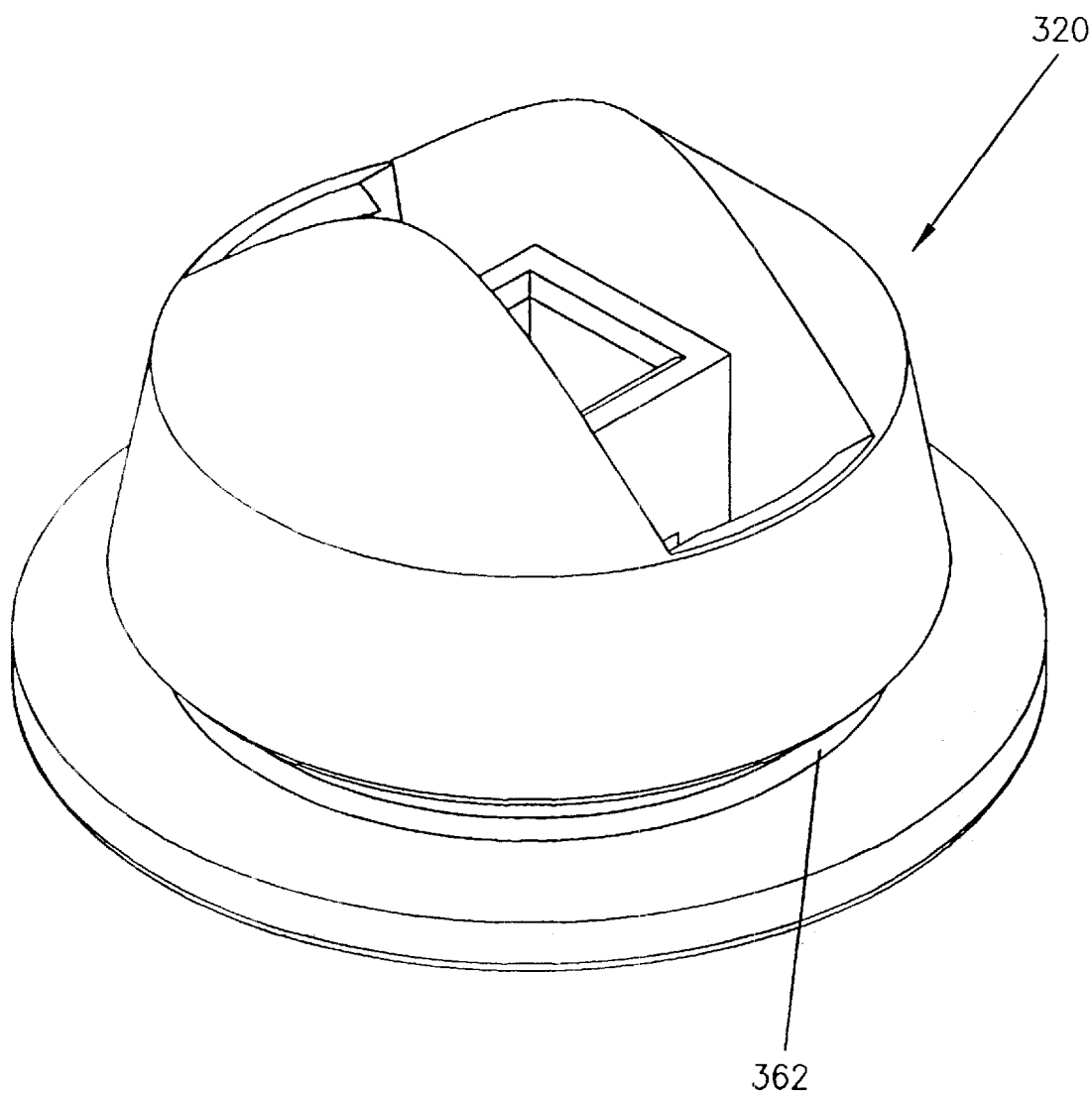
FIG. 12B illustrates an elevational view of a first base member of a two-piece base for use with the cover surface of FIG. 12A.
Figure 12C:
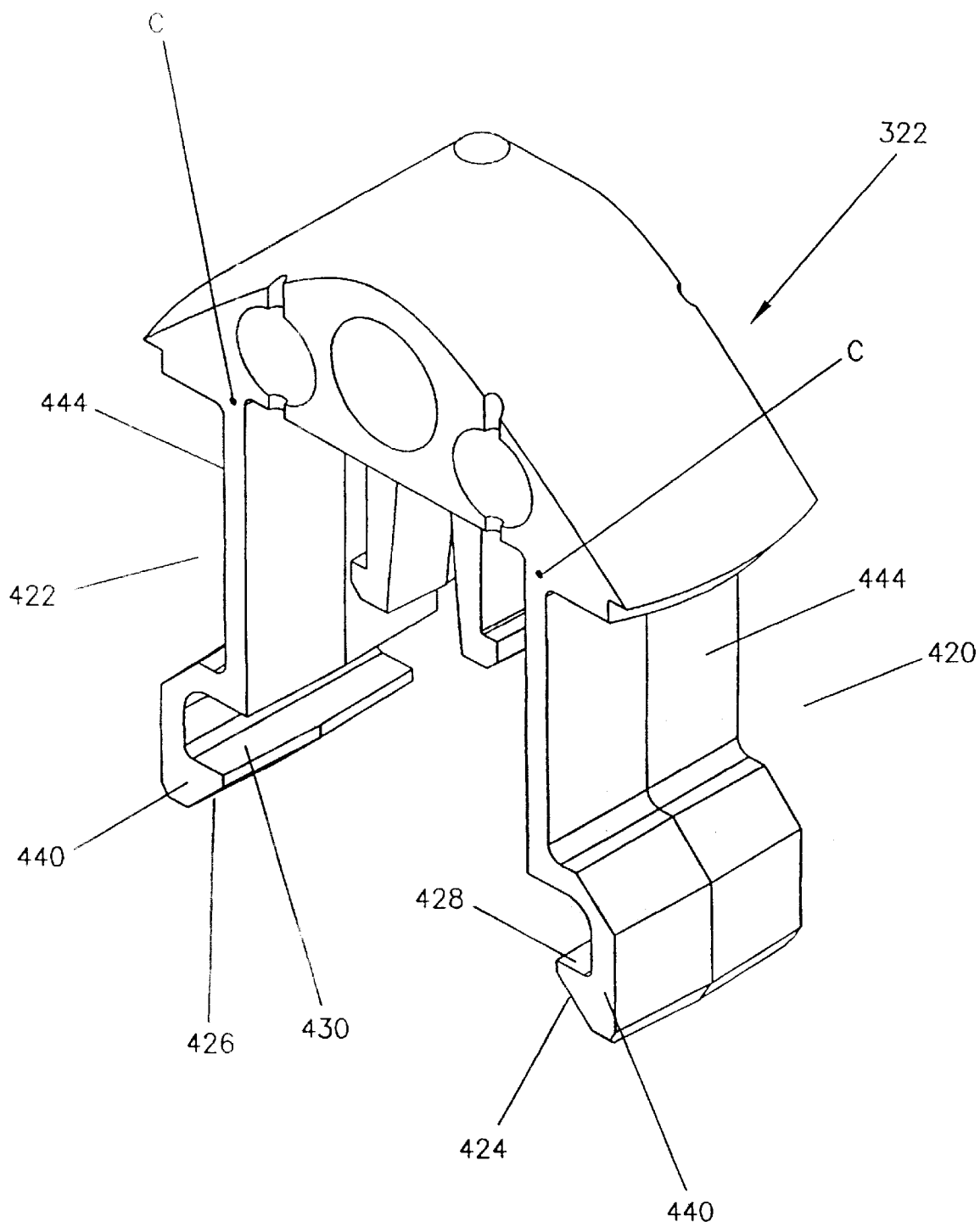
FIG. 12C illustrates an elevational view of a second base member (central yoke member) of the two-piece base for use with the first base member of FIG. 12B.
Figure 13A:
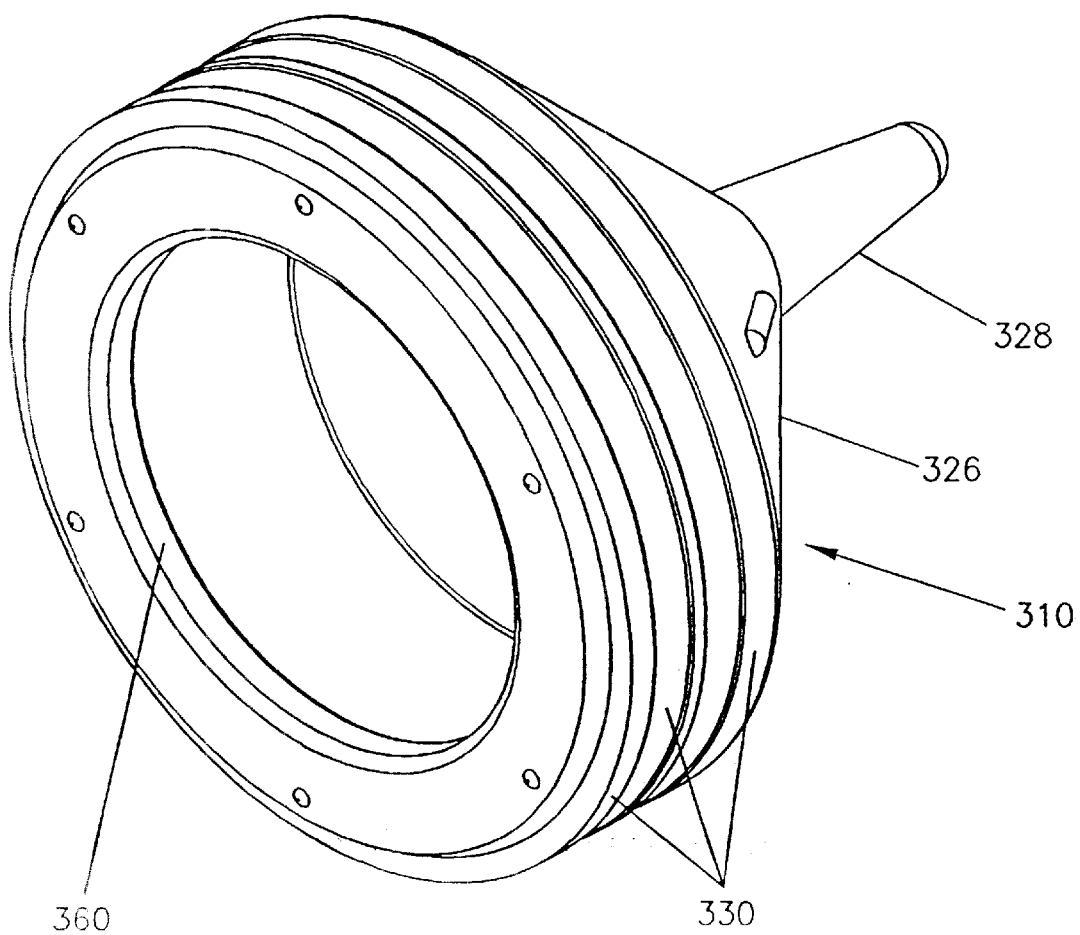
FIG. 13A illustrates a perspective view of the cover surface of FIG. 12A.
Figure 13B:
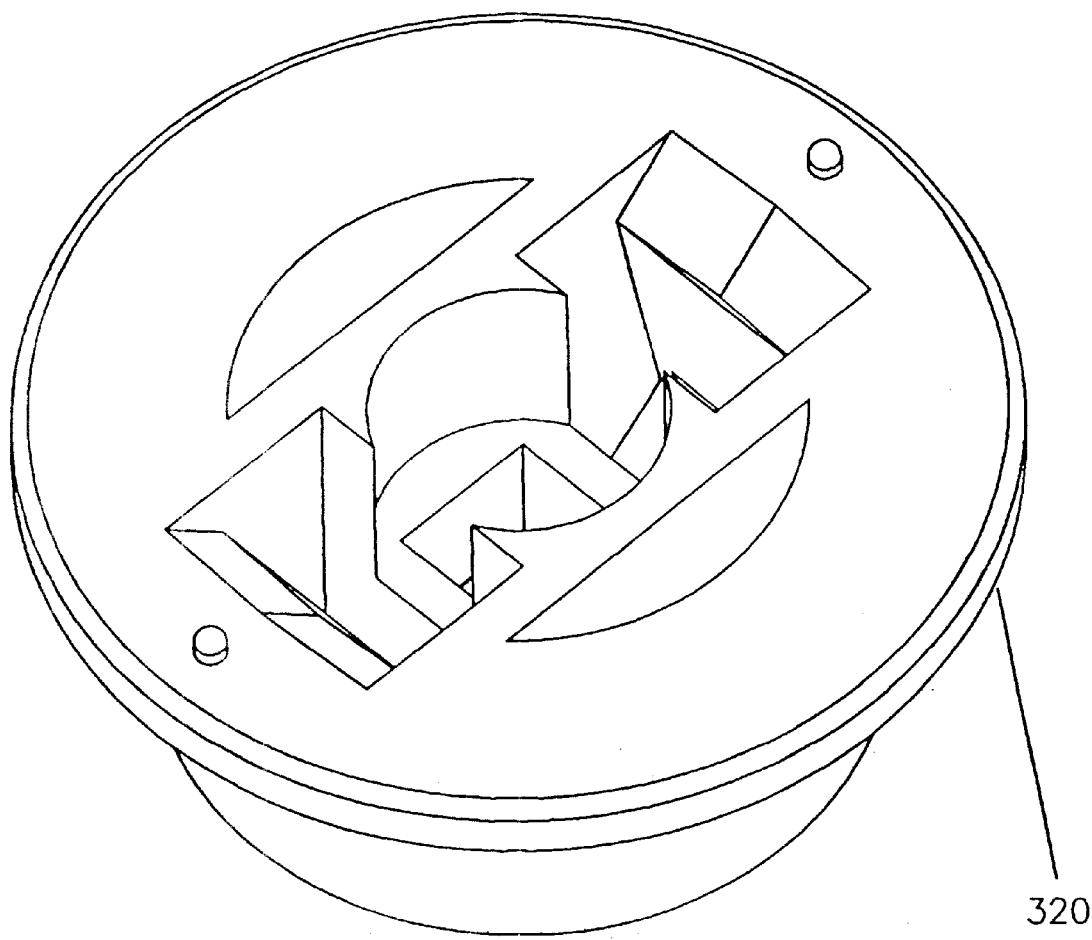
FIG. 13B illustrates a bottom perspective view of the first base member of FIG. 12B.
Figure 13C:
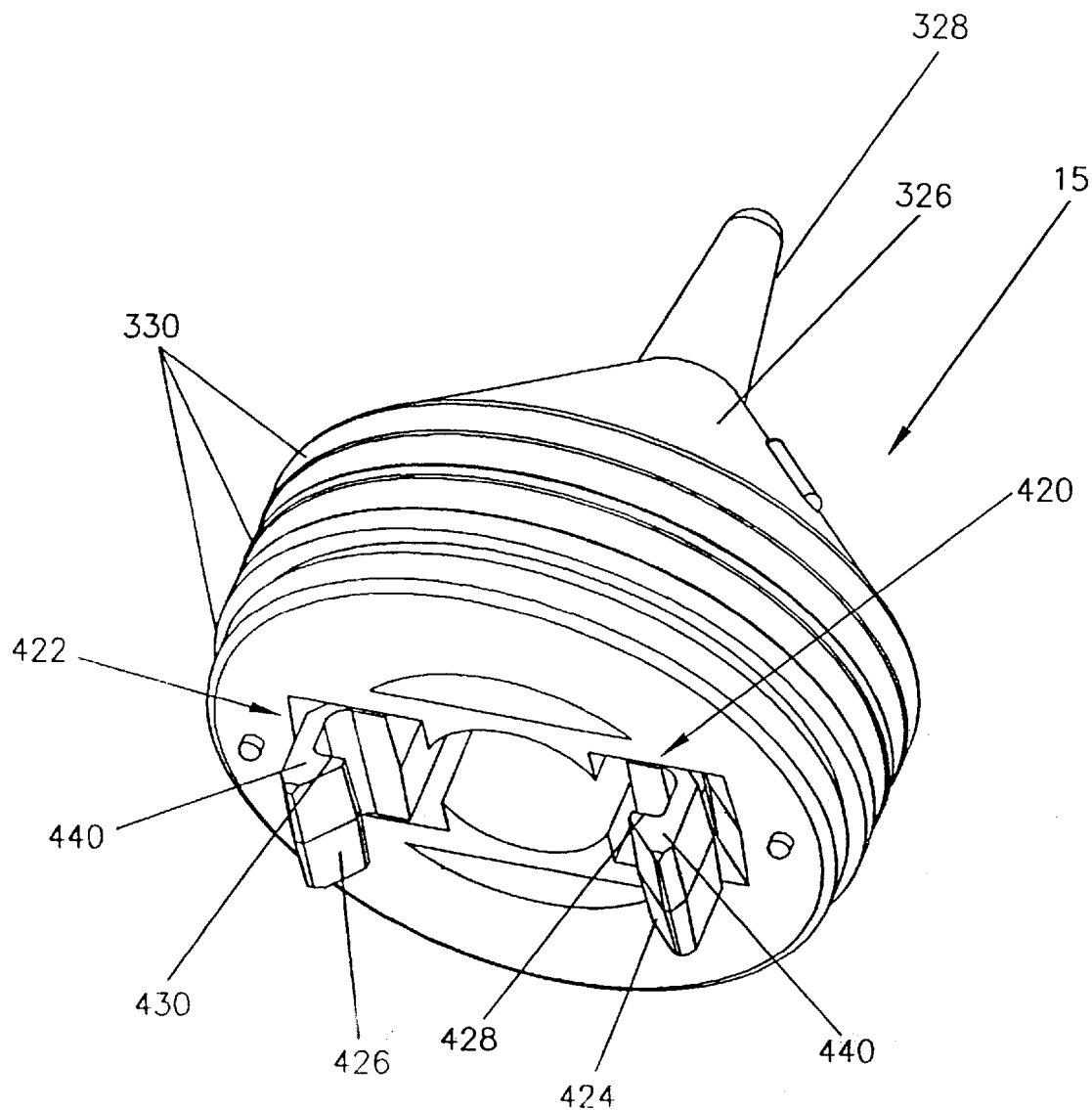
FIGS. 13C illustrates a perspective view of an assembled plunger of the present invention.

Visual indications that syringe 10' is properly secured may also be provided. For example, and as best illustrated in FIG. 8, a pair of indicator arrows 180 and 182 are preferably formed on a forward surface 184 of drip flange 62'. When syringe 10' has been fully locked into place in opening 26' of retainer 25', indicator arrows 180 and 182 are preferably in alignment with suitable visual indicators 186 and 188 (see FIG. 4) preferably formed on the front face of injector front wall 28.

Preferably, projection 156 is formed at the same angular location as indicator arrow 180, while projection 158 is formed at the same angular location as indicator arrow 182. In this manner indicator arrows 180 and 182 provide a visual indication of the position of projections 156 and 158 as syringe 10' is rotated into place.

Figure 9:
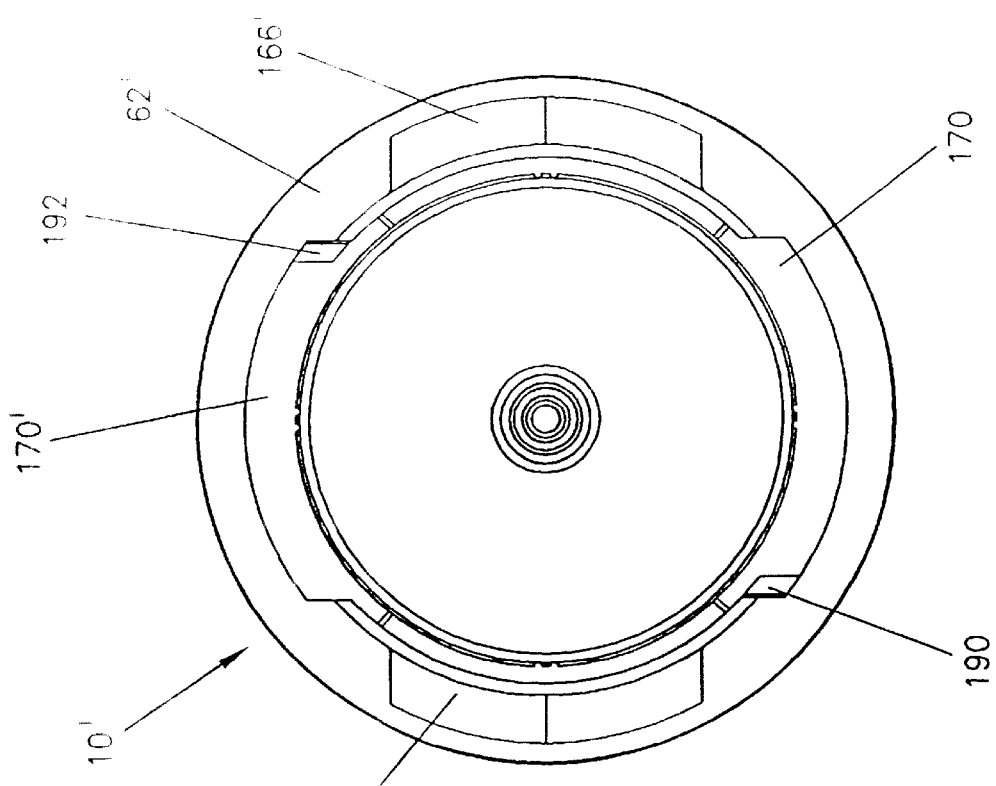
FIG. 9 illustrates a rear view of the syringe of FIG. 7A.

Syringe 10' and injector 20' are preferably further provided with cooperating data exchange mechanisms for exchanging information between syringe 10' and injector 20'. As best illustrated in FIG. 9, for example, third mounting flanges 170 and 170' may be provided with recesses or depressions 190 and 192, respectively, formed therein to convey information concerning syringe 10' or its contents to the injector 20'. Varying the presence, type and/or location of such depressions may be used to encode information.

Figure 5:
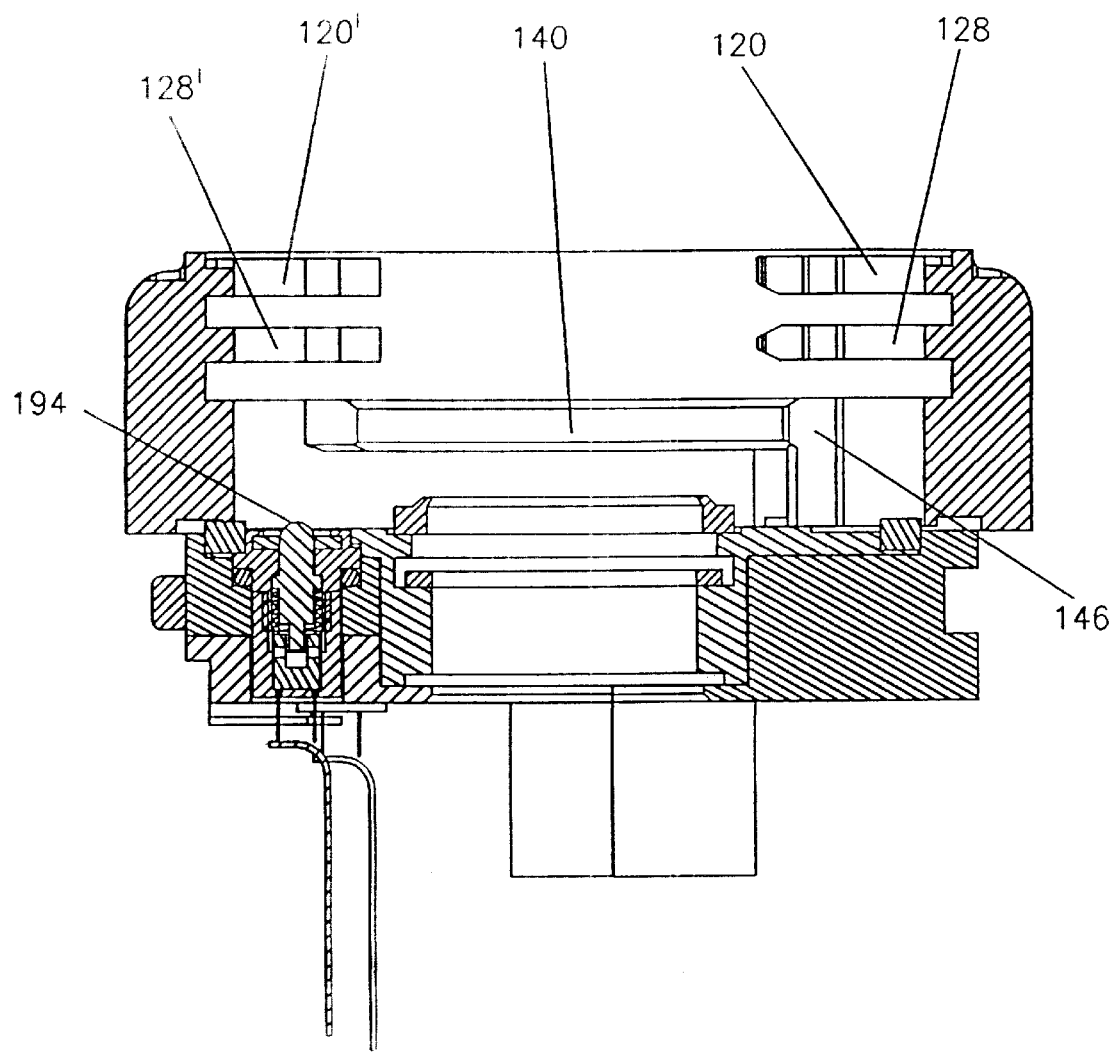
FIG. 5 illustrates a cross-sectional view of the front wall and a forward portion of the injector of FIG. 1B.

As illustrated in FIG. 5, a spring-actuated sensor switch 194 may be appropriately positioned to be activated by one of depressions 190 or 192 to indicate, for example, the type of syringe which has been installed, the identity of the fluid contained therein and/or the amount of fluid contained therein.

Similarly, other depressions may be selectively formed in substantially any area of any mounting flange, as long as the structural integrity of the mounting flanges is not compromised. Similar cooperating sensor elements can also be used to ensure full engagement of syringe 10'. For example appropriate logic may be provided in a manner clear to one of skill in the art such that without full engagement, injector piston 22 will not be actuated by the injector motor and no injection will take place. Cooperating depressions and sensor switches may also function in a timed mode, such that the sensor switches read information from a series of depressions as they are moved past the sensor switches by the action of rotating syringe 10' into place.

Figure 6A:
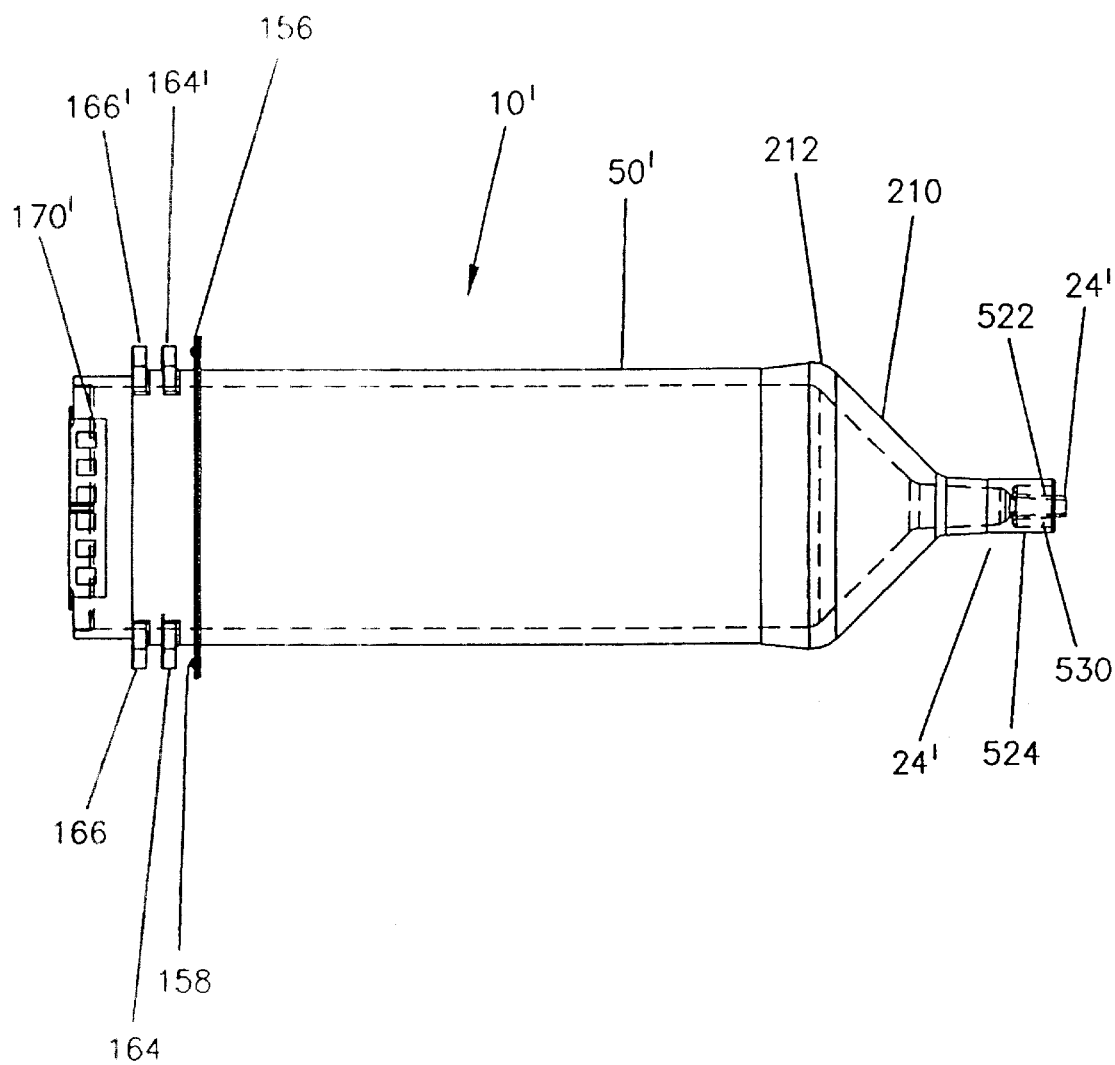
FIG. 6A illustrates a plan view of an embodiment of a syringe of the present invention.
Figure 7A:
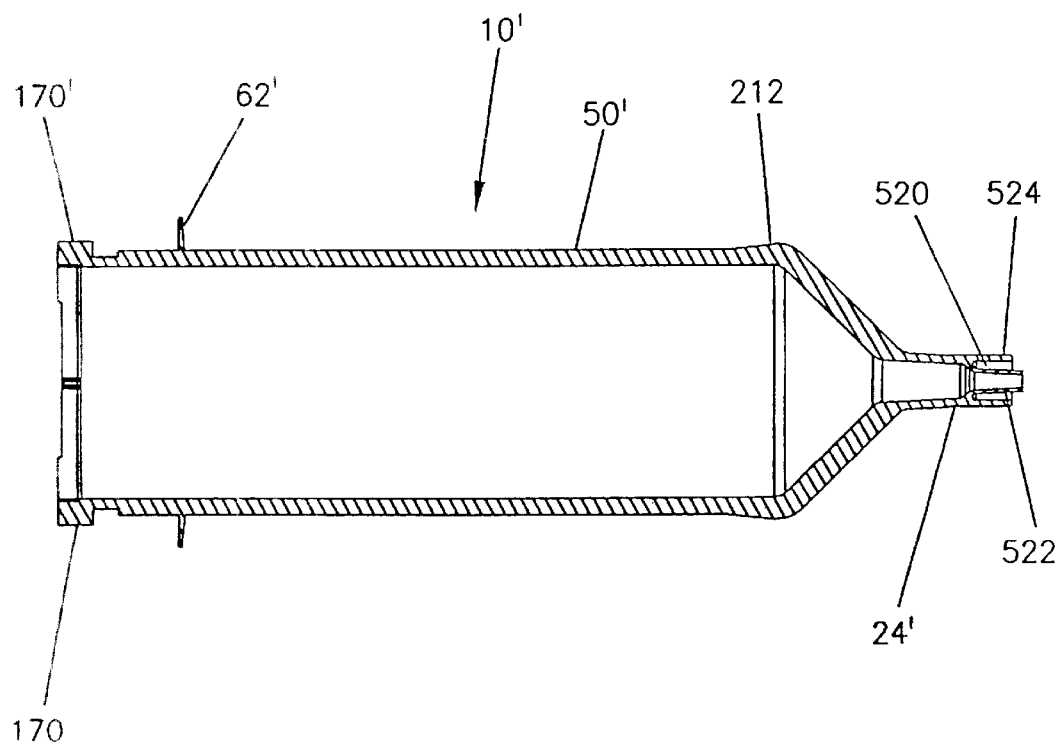
FIG. 7A illustrates a cross-sectional view of the syringe of FIG. 6A; 257
Figure 7B:
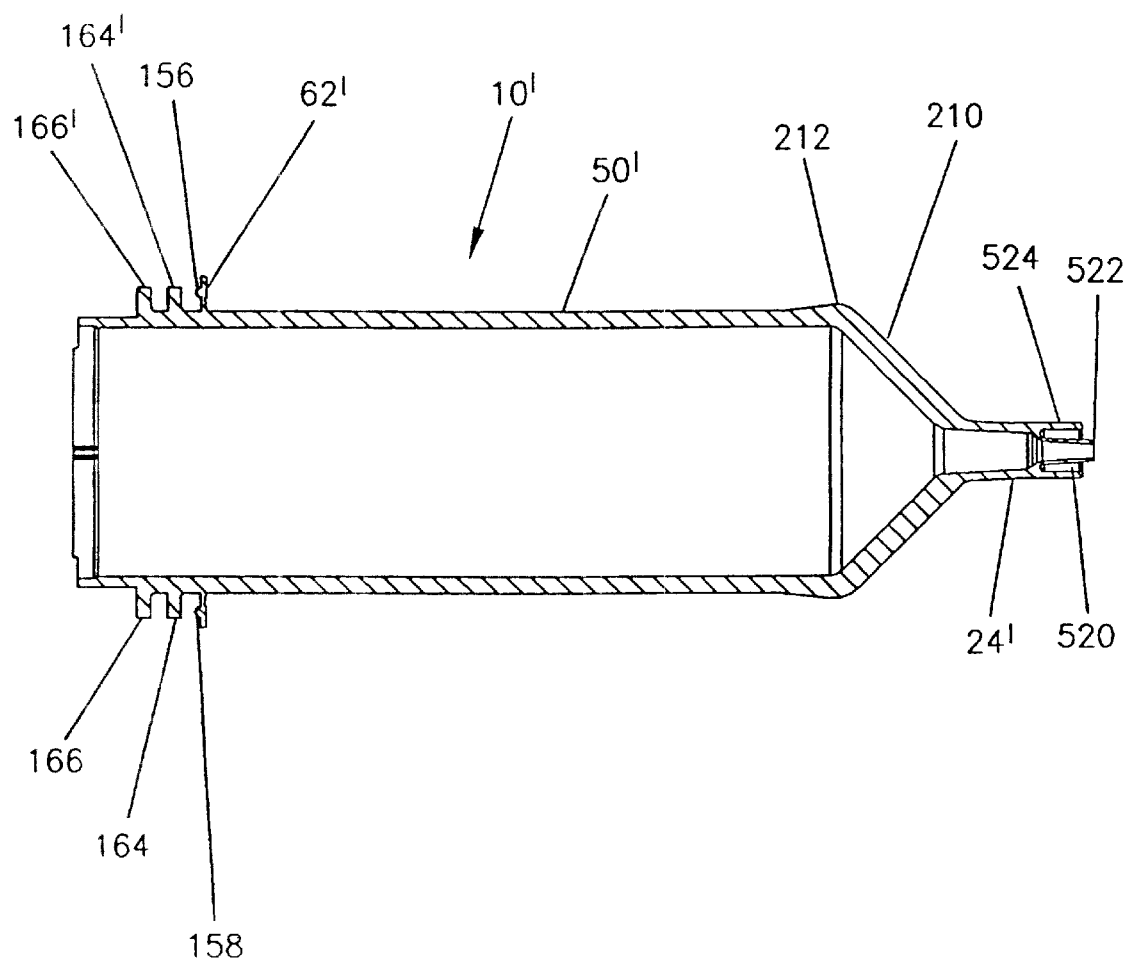
FIG. 7B illustrates a second, cross-sectional view of the syringe of FIG. 6A rotated approximately 90° from the view of FIG. 7A.

As illustrated in FIGS. 6A, 7A and 7B, the forward end of the syringe 10' preferably includes a conical transition region 210 that provides a transition between main cylindrical body 50' and syringe tip 24'. A corner or intersection 212 is formed between cylindrical main body 50' and conical portion 210 on the syringe 10'. Intersection 212 is a critical zone which is likely to fail under pressure more quickly than either of the sections it joins. For this reason, intersection 212 is preferably provided with means for reinforcing structural integrity in that area. In a preferred embodiment, the wall thickness in the vicinity of intersection 212 is greater than the general wall thickness of cylindrical main body 50'. Preferably, the wall thickness of the entire conical transition region 210 is likewise increased. Reinforcing the structural integrity of intersection 212 and conical transition region 210 enables the use of a number of materials (for example, which are chemically and biochemically compatible with the injection fluid) which would otherwise be unsuitable because of mechanical failure at high pressure.

Increasing the wall thickness of intersection 212 and conical transition region 210 reduces bending stress experienced during injection. Alternatively, but at increased fabrication cost, the wall thickness of syringe 10' may be uniformly increased throughout syringe 10' such that bending, meridianal, and circumferential (hoop) stresses are below the tensile yield stress of the syringe material used (or within the elastic region of the stress-strain curve).

Figure 6B:
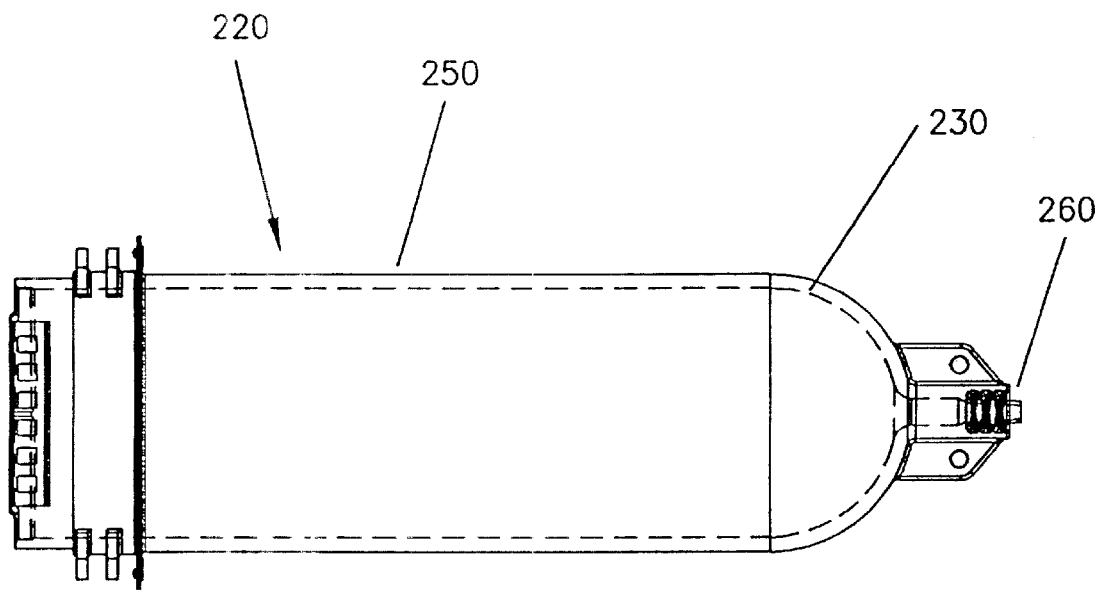
FIG. 6B illustrates a plan view of another embodiment of a syringe of the present invention.

FIG. 6B illustrates an embodiment of a syringe 220 in which the likelihood of failure under high internal pressure is decreased by providing a transition region 230 of a generally hemispherical shape to connect cylindrical main body 250 with syringe tip or injection region 260.

As best illustrated in FIGS. 11 through 13C, plunger 15, which is slidably disposed inside cylindrical main body 50', preferably comprises an elastomeric cover surface or sealing cover 310 and a base 312. In the case of a prefillable syringe, cover 310 is preferably injection-fluid-compatible (that is, chemically compatible and biochemically compatible with the injection fluid). Any contact with the injection fluid is preferably made only with cover 310 and, therefore, base 312 need not be fabricated from a long-term chemically and biochemically compatible material in the case of a prefillable syringe. Base 312 is preferably fabricated from a relatively structurally strong material such as a nylon or polycarbonate. In the embodiment illustrated in FIGS. 11 through 13C, for ease of fabrication base 312 comprises a first base member 320 and a second base member or yoke member 322. Base 312 can, however, be fabricated to be integral.

In the case of a prefillable syringe, sealing cover 310 of plunger 15 may comprise, for example, an elastomeric material such as a thermoplastic elastomer or a synthetic. Such elastomeric materials for sealing cover 310 preferably generally have a hardness in the range of approximately 50–60 Shore A, low compression set characteristic at elevated temperatures (for example, at autoclave temperatures), high chemical resistance and isotropic behavior. Moreover, such elastomeric materials should have no plasticizers and have very low levels of organic and metallic extractables.

Cover 310 preferably includes a forward portion 326 having the general shape of the inner wall of the transition region (for example, conical or hemispherical) of the syringe in which plunger 15 is to be used. Cover 310 also preferably includes a protuberance or nose 328 shaped to occupy at least a portion of syringe tip 24 when plunger 15 is in a forward position. Nose 328 decreases the amount of injection fluid which remains inside syringe 10' after plunger 15 is advanced forward to mate with, for example, conical transition region 210.

A side portion of cover 310 forms a cylindrical sealing engagement with the inner sidewall of cylindrical main body 50'. In a preferred embodiment, plunger cover 310 has a plurality of circumferential seal ribs 330 (preferably, at least three) which protrude from the outer perimeter of the cover 310 to more effectively create a seal between cover 310 and the inner sidewall of cylindrical main body 50' for the containment and storage of parenteral agents. Seal ribs 330 also assist in maintaining the position of the plunger assembly during autoclave processes. Plunger 15 is properly positioned within the syringe barrel 50 when plunger axis A (shown in FIG. 11) is parallel to barrel axis A (shown in FIG. 1A). A linear distance L between the leading edge of the forwardmost rib 330 of cover 310 and the trailing edge of the rearwardmost rib 330 of cover 310 is preferable at least 30% of the syringe internal diameter. Such an approximately 3:1 ratio limits misalignment of the plunger axis A and barrel axis A which may occur during the autoclave cycle.

In a preferred embodiment, sidewall 340 of base 312 has a slope or angle of taper represented by the angle $\Phi$ (see FIG. 11), which is preferably greater than approximately 0° and less that approximately 90° (as measured from the horizontal as depicted in FIG. 11). More preferably, $\Phi$ is in the range of approximately 3° to approximately 15°. Even more preferably, $\Phi$ is in the range of approximately 4° to approximately 10°. The rear diameter of sidewall 340 is thus greater than the forward diameter of sidewall 340, forming the general shape of a fulcrum. Cover 310 is preferably fabricated such that the thickness of a side engaging or seal portion 350 thereof is greater at the forward portion thereof than at the rearward portion thereof. Thus, while the slope or exterior sidewall of side engaging portion 350 of cover 310, which contacts the inner sidewall of cylindrical main body 50', is generally flat (that is, forming an angle of approximately 0° with the horizontal as illustrated in FIG. 11), the slope of the interior sidewall of engaging portion 350 is preferably approximately the same as the slope or angle of taper of sidewall 340 of base 312. A surface preparation or lubricant as known in the art, such as a silicone oil, is preferably provided between cover 310 and base 312 to facilitate relevant movement therebetween, thereby ensuring adequate dynamic function. The above construction of plunger 15 improves the sealing engagement between plunger 15 and the inner sidewall of cylindrical main body 50' of syringe 10' by minimizing the negative effects of compression set which may be experienced by some cover materials during sterilization. Further, this plunger construction assists in minimizing unwanted (and potentially irreversible) plunger movement during sterilization.

As the internal pressure of the syringe system increases, the elastomeric material in the region of 350 of seal cover 310 tends to slide along surface 340 of base 312 parallel to axis A of plunger 15. The sliding action of these components in response to increased internal syringe pressure forces seal cover 310 to exert a radial force on the inside wall of syringe barrel 50', thereby creating a dynamic "wedge" seal system.

In the case of "static" seal systems (for example O-rings), used on current syringe systems, as the internal syringe pressure increases, the radial expansion of the vessel must be minimal to ensure an adequate seal. Such static sealing systems are thus generally acceptable in a syringe barrel system where radial barrel growth is negligible. In a prefillable syringe system, however, radial growth in response to increases in internal pressure can be substantial due to the weakness of certain syringe materials, and the lack of a pressure jacket. For example, radial growth of the barrel 50 is typically observed under internal pressures achieved during a powered injection. The wedge dynamic seal provides a dynamic seal within such a relatively flexible, radially expanding syringe barrel under relatively high internal pressures.

As also best illustrated in FIG. 11, seal cover 310 preferably has an inwardly projecting circumferential attachment member 360. Attachment member 360 is designed to seat in a channel 362 of base 312 to hold seal cover 310 on base 312.

As discussed above, piston 22 cooperates with plunger 15 to impart reciprocal motion thereto. Piston 22 preferably comprises a stem 410 and a piston head 412 formed on a distal end of stem 410. Piston head 412 preferably extends radially outwardly beyond the radial edge of stem 410. In the embodiment illustrated in FIG. 1A through 2B, piston head 412 comprises two opposing piston flanges 414 and 416.

Base 312 of plunger 15 preferably includes capture members 420 and 422 protruding rearwardly beyond the rear surface of base 15 by an amount sufficient to capture and retain flanges 414 and 416 of the piston head 412 (see, for example, FIG. 2B). Capture members 420 and 422 are preferably constructed of a flexible material such that capture members 420 and 422 flex radially outwardly when contacted by piston flanges 414 and 416 and subsequently "snap back" to capture piston flanges 414 and 416. While only two capture members 414 and 416 are shown, as clear to one skilled in the art, more than two capture members 414 and 416 can be used with a corresponding change in the shape of the piston head 412.

In a preferred embodiment, as piston 22 moves forward to contact plunger 15 a pair of preferably beveled surfaces 424 and 426 are aligned with and engaged by piston flanges 414 and 416 and are forced radially outwardly until piston head flanges 414 and 416 pass beyond and over inner shoulders 428 and 430. This design enables piston 22 to engage plunger 15 easily at any axial position of plunger 15, thus permitting use of various injection liquid fill volumes in syringes. In a preferred embodiment, beveled surfaces 424 and 426 are aligned for engagement with piston flanges 414 and 416 when syringe 10' is properly mounted in retainer 25'. Likewise, disengaging rotation of capture members 420 and 422 relative to piston 22 preferably corresponds to the rotation of syringe 10' required to dismount syringe 10' from retainer 25' so that plunger 15 (which preferably rotates with syringe 10') is disengaged from piston head 412 when syringe 10' is rotated and dismounted from retainer 25'.

In another embodiment, capture members 420 and 422 can be fabricated to be substantially rigid and piston flanges 414 and 416 (shown in FIG. 1A) can be fabricated to be flexible or spring-loaded such that piston flanges 414 and 416 deflect radially inwardly (with respect to axis A) to allow passage of piston head 412 between capture members 420 and 422 and retention of piston head 412 by capture members 420 and 422.

After retention of piston head 412 by capture members 420 and 422, plunger 15 preferably resists disconnection from piston 22 upon rearward movement of piston 22. In one embodiment, capture members 420 and 422 are designed such that the forces exerted upon capture members 420 and 422 upon rearward movement of piston 22 substantially prevent radially outward deflection (or bending) of capture members 420 and 422. In the embodiment (best illustrated in FIG. 11), for example, retention members 440 of capture members 420 and 422 are positioned such that the load experienced upon rearward movement of piston 22 (represented by arrow F) is experienced at a position equal or greater in radial distance (relative to axis A) than points C where stems 444 of cantilevered capture members 420 and 422 are attached to base 312. The bending moment created by rearward motion of piston 22 thus tends to cause capture members 420 and 42' to deflect radially inwardly and assists in preventing disconnection of plunger 15 from piston 22.

Figure 14:
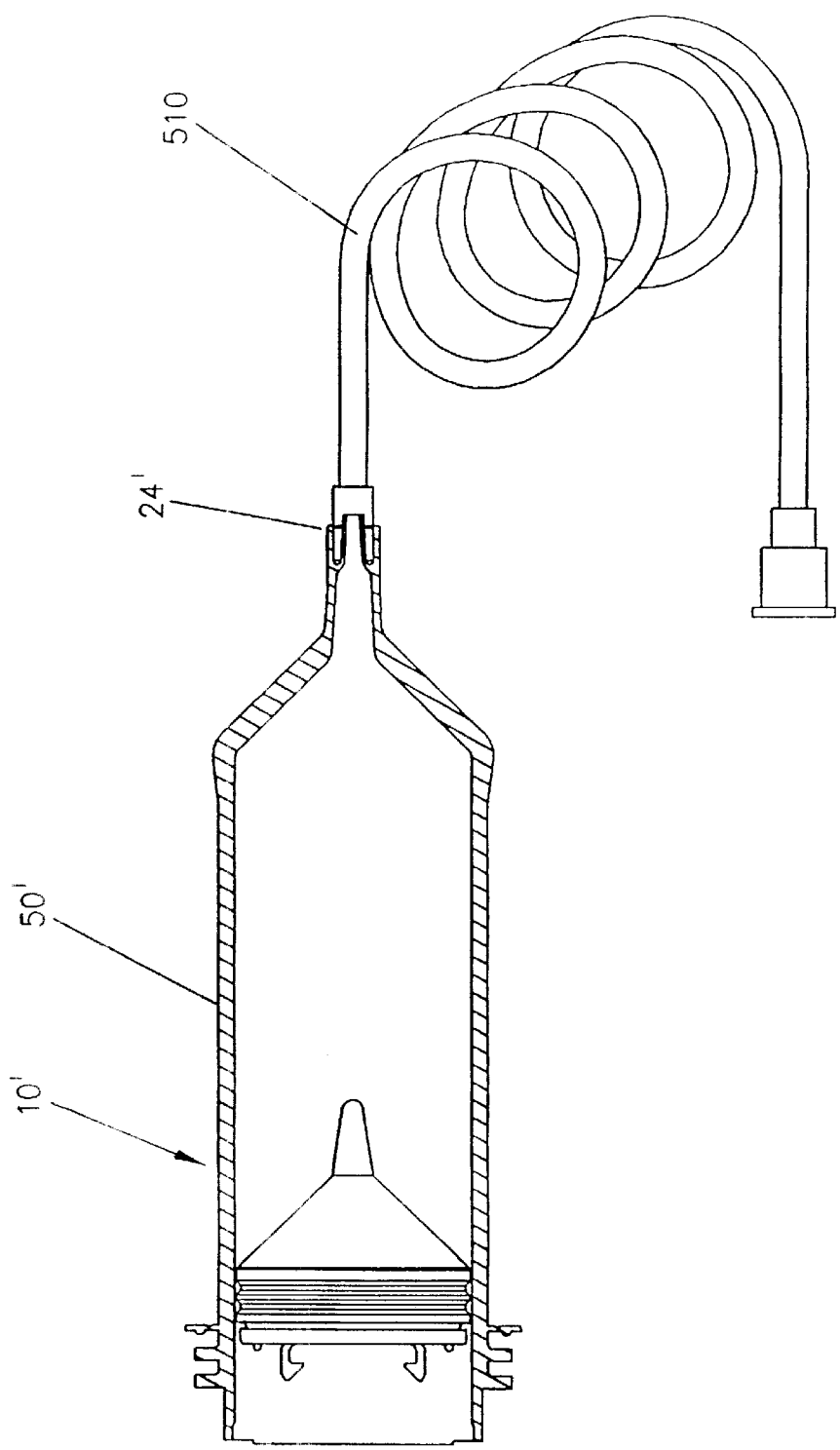
FIG. 14 illustrates a prefilled syringe including a connector tube.

During use, syringe 10', for example, is attached to a connecting tube which transports the injection fluid as known in the art to a hollow needle or the like inserted into the patient. As illustrated in FIG. 14, a prefilled syringe 10' may be provided as a unit with a connecting tube 510. In this embodiment, connecting tube 510 and syringe 10' are permanently affixed (for example, via an adhesive) to each other at syringe tip 24'. This joined nature allows both syringe 10' and tube 510 to be filled as a unit with an injection fluid, filling the entire volume of connecting tube 510 and a predetermined portion of elongated cylindrical main body 50'.

Syringe tip 24' may be terminated in any one of several manners. In the embodiment of syringe 10' illustrated in FIGS. 6A, 7A and 7B, for example, syringe tip 24' terminates in a standard male luer connection 520. Luer connection 520 comprises an inner tubular member 522 designed to mate with a standard female luer connector (not shown) on the flexible connector tube 510 as illustrated in FIG. 14. Syringe tip 24' also comprises a threaded outer wall 524 having an interior diameter that grips the luer connector of connector tube 510. Outer wall 524 preferably comprises a double-start, right-hand threaded luer lock fitting.

Figure 15:
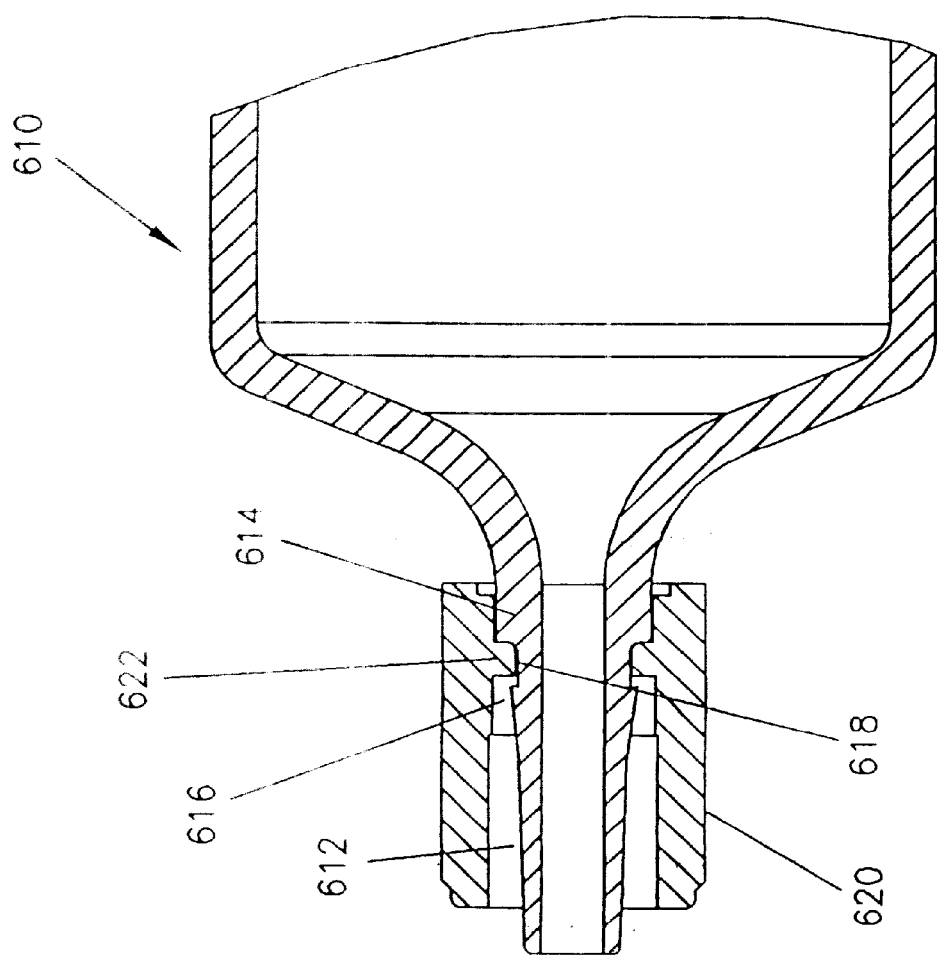
FIG. 15 illustrates an enlarged cross-sectional view of an embodiment of a swivel nut and syringe tip.

In another embodiment illustrated in FIG. 15, a syringe 610 is terminated in a long, relatively thin tube section 612 which preferably has a standard luer taper. Tube 612 preferably includes an annular channel 614 extending radially inwardly from the generally cylindrical exterior surface of tube section 612.

A generally cylindrical swivel nut 620 preferably comprises a radially inwardly projecting engaging flange 622. The width of retaining flange 622 is slightly smaller than the width of channel 614. Swivel nut 620 is preferably manufactured from a relatively tough and resilient material such as polycarbonate and preferably includes a series of exterior ribs 624 to aid the user in gripping and rotating swivel nut 620. Ribs 624 preferably extend in a direction parallel to the axis around which the syringe 610 is formed.

To attach swivel nut 620 to syringe 610, swivel nut 620 is placed over tube 612 and moved rearwardly, applying sufficient force to swivel nut 620, to cause retaining flange 622 to snap over retaining flange 616 to seat in channel 614. Further rearward movement of swivel nut 620 is prevented by a second retaining flange 618. Once swivel nut 620 has been snapped into place with respect to channel 614, it may rotate freely with respect to the syringe tube 612.

Figure 16:
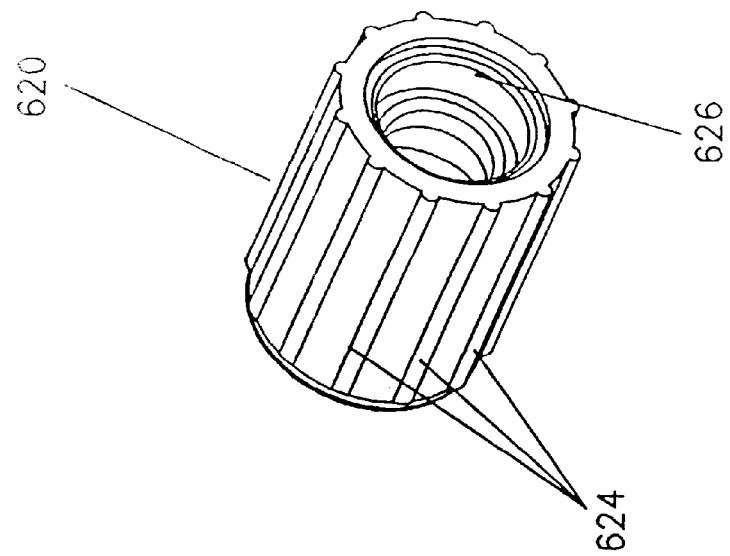
FIG. 16 illustrates a perspective view of the swivel nut of FIG. 15.

As best illustrated in FIG. 16, swivel nut 620 preferably comprises a plurality of interior threads 626 for engagement of the outside flange of a female luer fitting positioned at the end of an elastomeric connector tube. Preferably, threads 626 are double start right-handed threads (for example, according to MD-70 standards). In use, swivel nut 620 is simply rotated to screw onto a connector tube which occupies the space between the exterior sidewall of tube 612 and threads 626.

Figure 17:
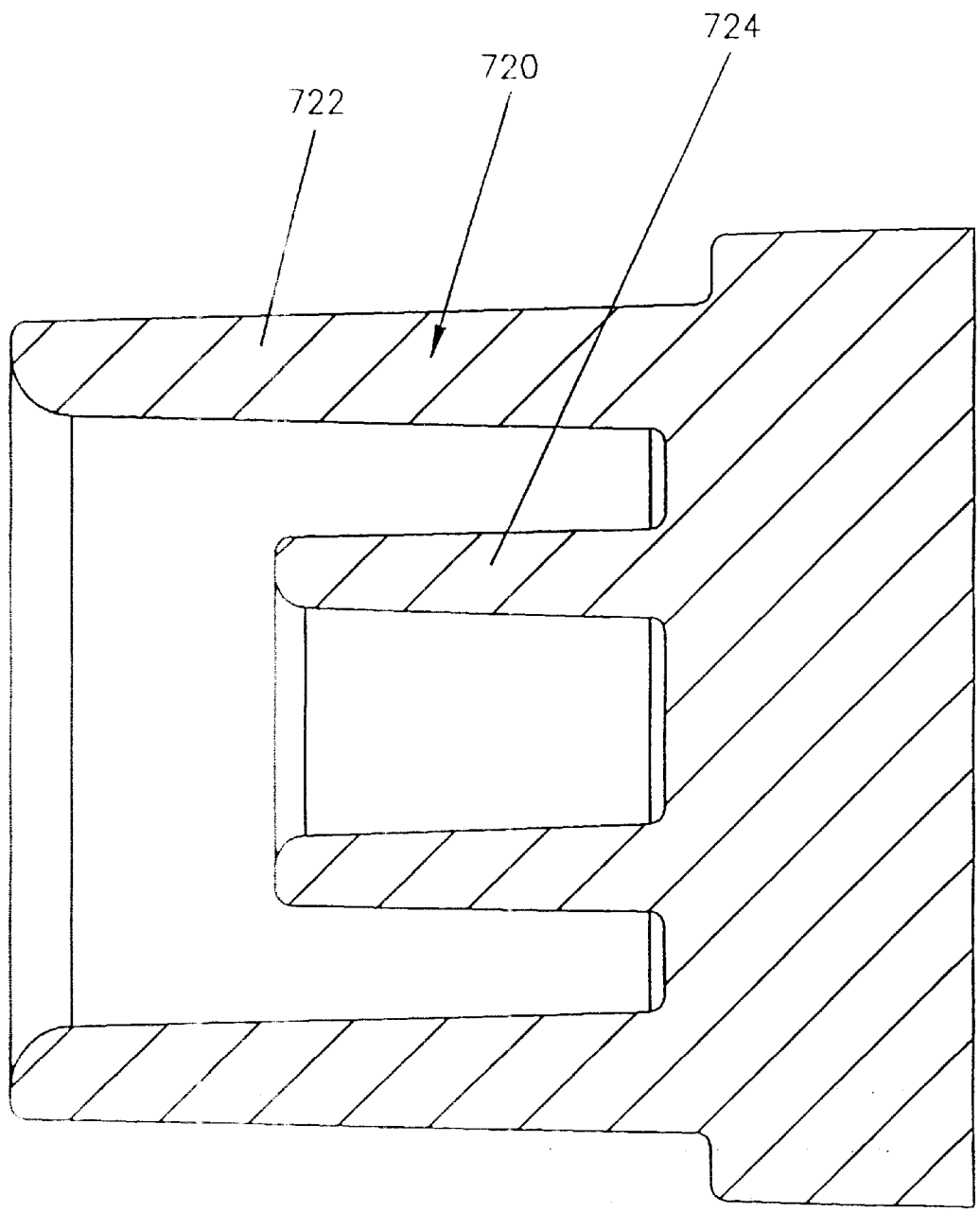
FIG. 17 illustrates a cross-sectional view of an embodiment of a tip seal.

FIG. 17 is a cross-sectional illustration of a syringe tip seal 720 which is fluid-tight with respect to the injection fluid within a syringe. The embodiment of tip seal 720 illustrated in FIG. 17 is designed for use, for example, with a syringe tip terminating in a standard luer fitting as illustrated in FIGS. 6A, 7A, 7B and 14. Tip seal 720 is preferably fabricated from an elastomeric material that is chemically and biochemically compatible with the injection fluid. For example, tip seal 720 may be fabricated from a thermoplastic elastomer or synthetic halobutyl isoprene. Tip seal 720 preferably comprises an outer, generally cylindrical, seal member 722. Seal member 722 preferably has a tapered inner surface which forms a seal with the outer diameter of outer wall 524 of luer connection 520. Tip seal 720 also preferably comprises an inner, generally cylindrical, seal member 724. Inner seal member 724 preferably comprises a tapered inner surface which forms a seal with the outer diameter of inner tubular member 522 of luer connection 520.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A plunger for use in a syringe, the plunger comprising:
   a plunger surface including a seal portion contacting an inner wall of the syringe and forming a seal therewith; and
   a base over which the plunger surface is placed, the base including a side portion having a angle of taper wherein the diameter of the side portion decreases from a rearward axial position to a forward axial position thereof, the diameter of an inner wall of the seal portion of the plunger surface decreasing from rearward to a forward axial position at an angle approximately equal to the angle of taper of the side portion of the base, the side portion of the base and the seal portion creating a dynamic seal with increases of internal pressure within the syringe.

2. The plunger of claim 1 wherein the angle of taper is in the range of approximately 3° to approximately 15°.

3. The plunger of claim 2 wherein the angle of taper is in the range of approximately 4° to approximately 10°.

4. The plunger of claim 1, further comprising a forward portion having the general shape of an inner wall of a transition region of the syringe.

5. The plunger of claim 4 wherein the forward portion has a generally conical shape.

6. The plunger of claim 4 wherein the forward portion has a generally hemispherical shape.

7. A syringe comprising:
   a main body, an injection region having a smaller diameter than the main body, and a transition region connecting the main body and the injection region; and
   a plunger including a plunger surface having a seal portion contacting an inner wall of the main body of the syringe and forming a seal therewith, the plunger further including a base over which the plunger surface is placed, the base comprising a forward base portion having generally the shape of the forward portion of the plunger surface, the base further comprising a side portion having a angle of taper wherein the diameter of the side portion decreases from a rearward axial position to a forward axial position thereof, the diameter of an inner wall of the seal portion of the plunger surface decreasing from a rearward to a forward axial position at an angle approximately equal to the angle of taper of the side portion of the base, the side portion of the base and the seal portion creating a dynamic seal with increases of internal pressure within the syringe.

8. The syringe of claim 7 wherein the angle of taper is in the range of approximately 3° to approximately 15°.

9. The syringe of claim 8 wherein the angle of taper is in the range of approximately 4° to approximately 10°.

10. The syringe of claim 7, further comprising a forward portion having the general shape of an inner wall of the transition region of the syringe.

11. The syringe of claim 10 wherein the forward portion has a generally conical shape.

12. The syringe of claim 10 wherein the forward portion has a generally hemispherical shape.

13. A plunger for use in a syringe for injecting a liquid, the syringe comprising a main body, an injection region having a smaller diameter than the main body, and a transition region connecting the main body and the injection region, the plunger comprising:
   a plunger surface including a forward portion in contact with the liquid, the forward portion having the general shape of an inner wall of the transition region, the plunger surface further including a seal portion contacting an inner wall of the main body and forming a seal therewith, the plunger surface further including a protruding member at a forward end of the forward portion, the protruding member being adapted to enter the injection region of the syringe when the plunger is advanced to expel liquid in the injection region.

14. A syringe comprising:
   a main body having a first diameter;

an injection region having a second diameter smaller than the first diameter of the main body;

a transition region connecting the main body and the injection region; and a plunger movably disposed within the main body, the plunger comprising a plunger surface including a forward portion in contact with a liquid disposed in the syringe, the forward portion having the general shape of an inner wall of the transition region, the plunger surface further comprising a seal portion contacting an inner wall of the main body and forming a seal therewith and a protruding member at a forward end of the forward portion, the protruding member being adapted to enter the injection region of the syringe when the plunger is advanced to expel the liquid in the injection region.

15. The plunger of claim 13, further comprising at least one capture member projecting rearwardly from a rear surface of the plunger, the at least one capture member operable to form a releasable engagement with an injector drive member.

16. The syringe of claim 14, further comprising at least one capture member projecting rearwardly from a rear surface of the plunger, the at least one capture member operable to form a releasable engagement with an injector drive member.

* * * * *